United States Patent
Saitoh

(10) Patent No.: US 9,290,597 B2
(45) Date of Patent: Mar. 22, 2016

(54) (METH)ACRYLATE COMPOUND, OPTICAL COMPOSITION, MOLDED ARTICLE, AND OPTICAL ELEMENT

(71) Applicant: CANON KABUSHIKI KAISHA, Tokyo (JP)

(72) Inventor: Terunobu Saitoh, Hachioji (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/413,134

(22) PCT Filed: Jul. 24, 2013

(86) PCT No.: PCT/JP2013/070673
§ 371 (c)(1),
(2) Date: Jan. 6, 2015

(87) PCT Pub. No.: WO2014/021355
PCT Pub. Date: Feb. 6, 2014

(65) Prior Publication Data
US 2015/0175731 A1    Jun. 25, 2015

(30) Foreign Application Priority Data
Jul. 30, 2012    (JP) .................. 2012-168135

(51) Int. Cl.
| | |
|---|---|
| G02B 3/00 | (2006.01) |
| G02B 5/20 | (2006.01) |
| C08F 222/24 | (2006.01) |
| G02B 1/04 | (2006.01) |
| C07C 317/22 | (2006.01) |

(52) U.S. Cl.
CPC .............. *C08F 222/24* (2013.01); *C07C 317/22* (2013.01); *G02B 1/04* (2013.01); *G02B 1/041* (2013.01); *C08F 2222/245* (2013.01)

(58) Field of Classification Search
CPC .... C08F 222/24; C08F 222/12; C08F 222/10; G02B 1/00; G02B 1/04
USPC .................. 359/642; 252/582–589; 428/141; 522/90, 99; 523/102, 105, 107, 106, 523/120, 200, 206, 210, 322, 351, 400, 440, 523/443, 451, 458, 466; 524/100, 105, 106, 524/108, 109, 115, 120, 130, 143, 147, 161, 524/165, 188, 197, 199, 236, 261, 267, 284, 524/285, 317, 322, 323, 37, 392, 394, 396, 524/40, 400, 403, 406, 413, 418, 419, 420, 524/423, 425, 428, 430, 437, 442, 444, 492, 524/548, 554, 556, 588, 561, 570, 577, 600, 524/601, 606, 607, 609, 706, 709, 717, 720, 524/765, 770, 780, 787, 789, 81, 847, 849, 524/862, 91, 94, 96
See application file for complete search history.

(56) References Cited

U.S. PATENT DOCUMENTS

| | | |
|---|---|---|
| 5,479,555 A | 12/1995 | Rot et al. |
| 8,344,094 B2 | 1/2013 | Iwasa et al. |
| 8,569,541 B2 | 10/2013 | Saitoh |
| 8,829,230 B2 | 9/2014 | Saitoh |
| 2008/0200582 A1 | 8/2008 | Craciun et al. |
| 2011/0288330 A1* | 11/2011 | Saitoh ........................ 560/194 |

FOREIGN PATENT DOCUMENTS

| | | |
|---|---|---|
| CN | 102260201 A | 11/2011 |
| EP | 2 390 684 A2 | 11/2011 |
| JP | 2010-519369 A | 6/2010 |
| JP | 2011-178985 A | 9/2011 |

OTHER PUBLICATIONS

Office Action in Chinese Application No. 201380040464.9 (dated Aug. 7, 2015).

* cited by examiner

*Primary Examiner* — James Greece
(74) *Attorney, Agent, or Firm* — Fitzpatrick, Cella, Harper & Scinto

(57) ABSTRACT

An optical element including a molded article is provided, the molded article being prepared by molding a polymer prepared by polymerizing a (meth)acrylate compound represented at least by the following general formula (1):

Formula 1

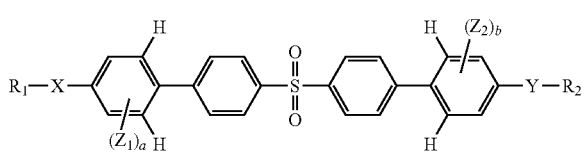
(1)

wherein a and b are each an integer of 1 or 2; X and Y are each —S— or —O—; $R_1$ and $R_2$ are each an alkyl group having 1 or 2 carbon atoms or a hydrogen atom; and $Z_1$ and $Z_2$ are each an alkyl group having 1 or 2 carbon atoms, having a substituent and represented by the following general formula (2):

Formula 2

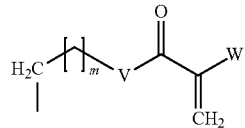
(2)

wherein m is selected from 0 and 1; W is a hydrogen atom or a methyl group; and V is selected from substituents represented by the following:

*—O—$C_nH_{2n}$—O—**;

*—S—$C_nH_{2n}$—S—**; and

*—S—$C_nH_{2n}$—O—**, wherein * represents a bond with an alkyl group; ** represents a bond with a (meth)acryloyl group; n is selected from 2, 3 and 4; and at least one hydrogen atom of —$C_nH_{2n}$— is replaced by a methyl group.

17 Claims, 2 Drawing Sheets

(METH)ACRYLATE COMPOUND, OPTICAL COMPOSITION, MOLDED ARTICLE, AND OPTICAL ELEMENT

TECHNICAL FIELD

The present invention relates to a (meth)acrylate compound, an optical composition, a molded article, and an optical element, and particularly to a (meth)acrylate compound having peculiar optical properties, and an optical composition, a molded article and an optical element using the (meth)acrylate compound.

BACKGROUND ART

Optical materials including glass materials, organic resins or the like generally exhibit a gradually higher refractive index on a shorter wavelength side. The indexes to indicate the wavelength dispersion of the refractive index include the Abbe number ($v_d$) and the secondary dispersion property ($\theta g, F$). The Abbe numbers and the $\theta g, F$ values are values peculiar to respective optical materials, but fall in certain ranges in many cases. FIG. 1 is a diagram illustrating the relationship between the secondary dispersion properties and the Abbe numbers of conventional optical materials (glass materials and organic resins). Here, the Abbe number ($v_d$) and the secondary dispersion property ($\theta g, F$) are represented by the following expressions. Abbe number $[v_d] = (n_d - 1)/(n_F - n_c)$, and Secondary dispersion property $[\theta g, F] = (n_g - n_F)/(n_F - n_c)$, where $n_d$ is a refractive index at a wavelength of 587.6 nm; $n_F$ is a refractive index at a wavelength of 486.1 nm; $n_c$ is a refractive index at a wavelength of 656.3 nm; and $n_g$ is a refractive index at a wavelength of 435.8 nm.

In dioptric systems, a suitable combination of glass materials having different dispersion properties generally enables reducing the chromatic aberration. For example, in an objective lens of a telescope or the like, the chromatic aberration emerging on an axis is corrected by using a combination of a glass material having a small dispersion as a positive lens and a glass material having a large dispersion as a negative lens. However, in the case where the configuration and the number of lenses are limited, in the case where the glass material to be used for lenses is limited, and in other cases, a sufficient correction of the chromatic aberration is very difficult in some cases. One of methods to solve such a problem is a method of utilizing a glass material having an anomalous dispersion property, and designing optical elements utilizing this method is being carried out.

In the case where an optical element is manufactured which is excellent in the chromatic aberration correction function and whose shape is an aspherical shape or the like, the molding or the like of an organic resin on a spherical glass or the like has a higher advantage in being excellent in the mass-productivity, moldability, versatility and weight reduction than the use of a glass material as a material for the manufacture. However, the optical property of conventional organic resins falls in a certain range as shown in FIG. 1 (secondary dispersion property ($\theta g, F$) is 0.700 or less), and few organic resins exhibit a peculiar dispersion property.

Since many of organic substances exhibiting a peculiar dispersion property construct a conjugate structure by a double bond, a benzene ring and the like, the molecular rigidity and orientation increase, and the possibility of generation of adverse effects including a rise in the melting point and an increase in the birefringence is high. In the case of molding a material having a high melting point and a material having a high birefringence due to a molecular orientation, the molding needs to be carried out after the materials are heated to melt the crystal and destroy the orientation. However, if a polymerizable compound is heated, since the reduction in the pot life is apprehended, a material is demanded which exhibits a peculiar dispersion property and can be molded by being heated as little as possible.

If a material having a high birefringence is used for an optical element of an image pickup system, since the imaging position largely shifts, a clear image is hardly obtained. Therefore, a material is demanded which exhibits a peculiar dispersion property and has a low birefringence. A recommended magnitude of the birefringence depends on optical systems to be used and the positions for incorporating the optical systems, but if the birefringence is lower than 0.001, the applicable range of the optical systems broadens.

In the above background, US2011/0288330 proposes that sulfone (meth)acrylate being an organic resin indicated as A in FIG. 1 has a higher secondary dispersion property (higher $\theta g, F$ property) than general-purpose organic resin materials.

Japanese Patent Application Laid-Open No. 2011-178985 proposes the introduction of a branched molecular structure in order to reduce the birefringence.

However, although the materials proposed in US 2011/0288330 have a high $\theta g, F$ value, any of the materials have a birefringence of 0.001 or more. Although the material proposed in Japanese Patent Application Laid-Open No. 2011-178985 has an effect of reducing the birefringence, the material has a low transmittance.

CITATION LIST

Patent Literature

PTL 1: US 2011/0288330
PTL 2: Japanese Patent Application Laid-Open No. 2011-178985

SUMMARY OF INVENTION

The present invention has been achieved in consideration of the above-mentioned background technology, and provides a molded article having a high dispersion property (Abbe number ($v_d$)) and secondary dispersion property ($\theta g, F$) of the refractive index, and having a low birefringence and a high property of the chromatic aberration correction function, and an optical element using the same. The present invention also provides a (meth)acrylate compound and an optical composition to provide the molded article. That is, the present invention relates to an optical element including a molded article, the molded article being prepared by molding a polymer prepared by polymerizing a (meth)acrylate compound represented at least by the following general formula (1).

Formula 1

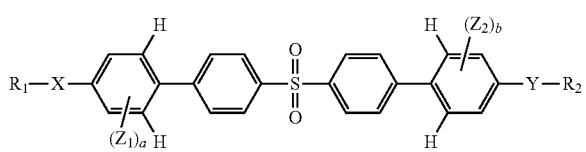

(1)

wherein a and b are each an integer of 1 or 2; X and Y are each —S— or —O—; $R_1$ and $R_2$ are each an alkyl group having 1 or 2 carbon atoms or a hydrogen atom; and $Z_1$ and $Z_2$ are each an alkyl group having 1 or 2 carbon atoms, having a substituent and represented by the following general formula (2).

Formula 2

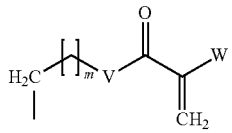

(2)

wherein m is selected from 0 and 1; W is a hydrogen atom or a methyl group; and V is selected from substituents represented by the following:

\*—O—$C_nH_{2n}$—O—\*\*;

\*—S—$C_nH_{2n}$—S—\*\*; and

\*—S—$C_nH_{2n}$—O—\*\*, wherein \* represents a bond with an alkyl group; \*\* represents a bond with a (meth)acryloyl group; n is selected from 2, 3 and 4; and at least one hydrogen atom of —$C_nH_{2n}$— is replaced by a methyl group. The present invention relates also to an optical composition including a (meth)acrylate compound represented at least by the following general formula (1) and a polymerization initiator.

Formula 1

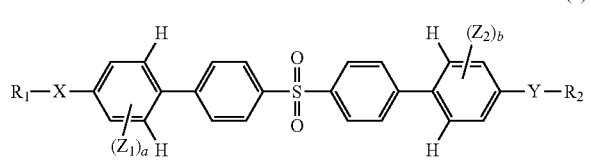

(1)

wherein a and b are each an integer of 1 or 2; X and Y are each —S— or —O—; $R_1$ and $R_2$ are each an alkyl group having 1 or 2 carbon atoms or a hydrogen atom; and $Z_1$ and $Z_2$ are each an alkyl group having 1 or 2 carbon atoms, having a substituent and represented by the following general formula (2).

Formula 2

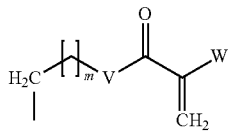

(2)

wherein m is selected from 0 and 1; W is a hydrogen atom or a methyl group; and V is selected from substituents represented by the following:

\*—O—$C_nH_{2n}$—O—\*\*;

\*—S—$C_nH_{2n}$—S—\*\*; and

\*—S—$C_nH_{2n}$—O—\*\*, wherein \* represents a bond with an alkyl group; \*\* represents a bond with a (meth)acryloyl group; n is selected from 2, 3 and 4; and at least one hydrogen atom of —$C_nH_{2n}$— is replaced by a methyl group. The present invention relates further to a (meth)acrylate compound represented at least by the following general formula (1).

Formula 1

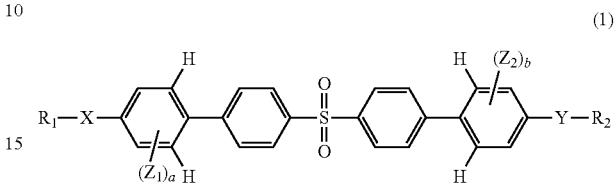

(1)

wherein a and b are each an integer of 1 or 2; X and Y are each —S— or —O—; $R_1$ and $R_2$ are each an alkyl group having 1 or 2 carbon atoms or a hydrogen atom; and $Z_1$ and $Z_2$ are each an alkyl group having 1 or 2 carbon atoms, having a substituent and represented by the following general formula (2).

Formula 2

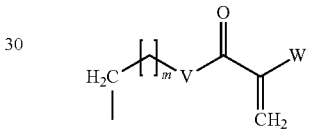

(2)

wherein m is selected from 0 and 1; W is a hydrogen atom or a methyl group; and V is selected from substituents represented by the following:

\*—O—$C_nH_{2n}$—O—\*\*;

\*—S—$C_nH_{2n}$—S—\*\*; and

\*—S—$C_nH_{2n}$—O—\*\*, wherein \* represents a bond with an alkyl group; \*\* represents a bond with a (meth)acryloyl group; n is selected from 2, 3 and 4; and at least one hydrogen atom of —$C_nH_{2n}$— is replaced by a methyl group.

Further features of the present invention will become apparent from the following description of exemplary embodiments with reference to the attached drawings.

DESCRIPTION OF EMBODIMENTS

Hereinafter, the present invention will be described in detail.

First, the (meth)acrylate compound and the optical composition according to the present invention will be described.

The optical composition according to the present invention includes a (meth)acrylate compound represented at least by the following general formula (1), and a polymerization initiator.

Formula 3

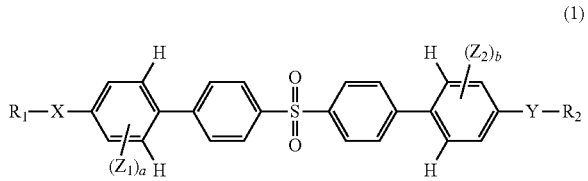

(1)

In the formula (1), a and b are each an integer of 1 or 2; when a is 2, two $Z_1$ may be identical or different, and when b is 2, two $Z_2$ may be identical or different; and in consideration of easiness of the synthesis, a and b can each be 1.

Figure 1:
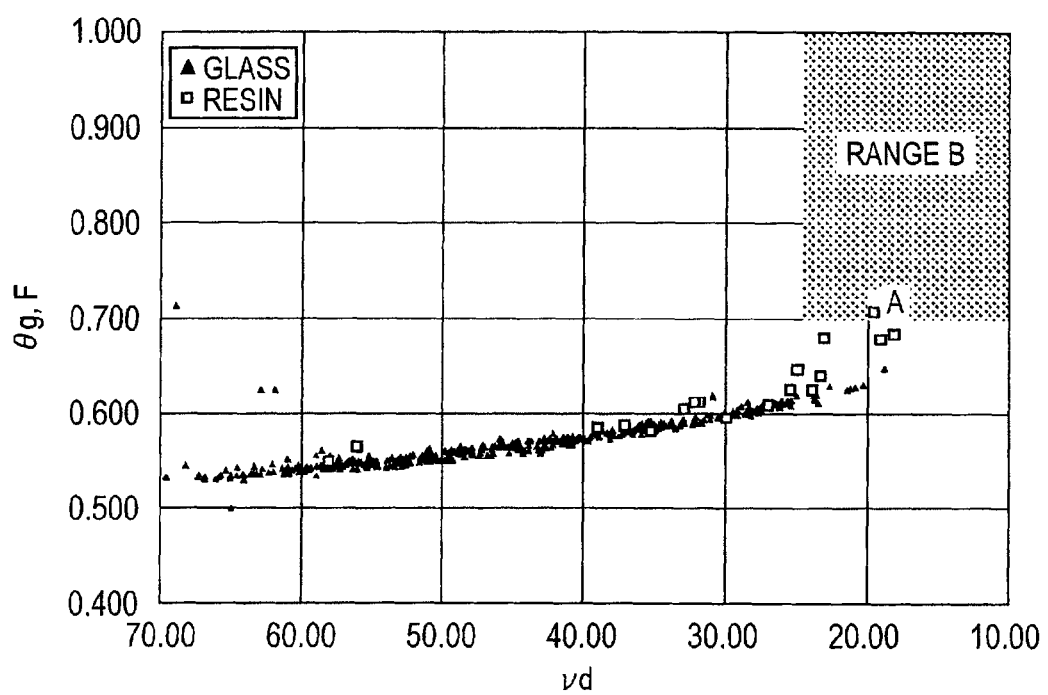
FIG. 1 is a graph illustrating the relationship between the secondary dispersion properties and the Abbe numbers of conventional optical materials.

Making X and Y to be electron-releasing elements makes good the state of the conjugate structure of the compound, and makes the optical property fall in the B region of FIG. 1. In consideration of easiness of the synthesis and stability of the compound, X and Y are each —S— or —O—. In consideration of easiness of procurement of raw materials, X and Y can each be —O—. In consideration of easiness of the synthesis, X and Y can be identical.

$R_1$ and $R_2$ are not especially limited as long as being substituents not deteriorating the optical property. $R_1$ and $R_2$ can each be an alkyl group having 1 or 2 carbon atoms or a hydrogen atom in order to suppress the deterioration of the optical property. $R_1$ and $R_2$ can be an alkyl group having 1 or 2 carbon atoms. The alkyl group having 1 or 2 carbon atoms is a methyl group or an ethyl group. $R_1$ and $R_2$ may be identical or different. $R_1$ and $R_2$ are desirably identical in consideration of easiness of the synthesis.

$Z_1$ and $Z_2$ are each an alkyl group having 1 or 2 carbon atoms, having a substituent and represented by the following general formula (2). The substituent is an alkoxy group, an alkylthio group or the like. In consideration of reduction of the birefringence and easiness of the synthesis, the alkyl group having 1 or 2 carbon atoms and having a substituent is a substituent represented by the following general formula (2). Here, the (meth)acryloyl group may be absent depending on the use form described later of the compound. In the case where the group is absent, the ** bond of V is a hydrogen atom.

Formula 4

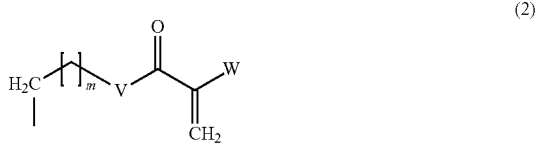

(2)

$Z_1$ and $Z_2$ may be identical or different. $Z_1$ and $Z_2$ are desirably identical in consideration of easiness of the synthesis. In the formula, m is not especially limited as long as not deteriorating the property of the compound. In consideration of easiness of procurement of raw materials, m is desirably one selected from 0 and 1. m is more preferably 0. W is not especially limited as long as not deteriorating the property of the compound and the reactivity of the polymerization reaction. W can be a hydrogen atom or a methyl group in consideration of the reactivity of the polymerization reaction and the easiness of procurement of raw materials.

V is desirably a substituent having at least one branch point in order to reduce the birefringence of a molded article including the optical composition. Having a branch point can more suppress the molecular orientation than compounds having no branch point, and enables reducing the birefringence. In order to suppress the deterioration of the optical property of an obtained molded article, V can be a substituent selected from substituents represented by the following:

\*—O—$C_nH_{2n}$—O—\*\*;

\*—S—$C_nH_{2n}$—S—\*\*; and

\*—S—$C_nH_{2n}$—O—\*\*, wherein \* represents a bond with an alkyl group; \*\* represents a bond with a (meth)acryloyl group; n is selected from 2, 3 and 4; and at least one hydrogen atom of —$C_nH_{2n}$— is replaced by a methyl group. The number of the methyl group substituted for the hydrogen atom can be 1 to 2 in order to suppress the deterioration of the optical property.

V can be a substituent shown below in consideration of easiness of the procurement of raw materials and the synthesis.

\*—O—$C_nH_{2n}$—O—\*\*

V more preferably includes —O—CH($CH_3$)—$CH_2$—O—, —O—$CH_2$—CH($CH_3$)—O—, —O—$CH_2$—CH($CH_3$)—$CH_2$—O— and —O—$CH_2$—C($CH_3$)$_2$—$CH_2$—O—.

One exemplary embodiment of a (meth)acrylate compound represented by the general formula (1) in the present invention can be a compound in which X and Y are each —S— or —O—; $R_1$ and $R_2$ are each an alkyl group having 1 or 2 carbon atoms; and $Z_1$ and $Z_2$ are each an alkyl group having 1 or 2 carbon atoms, having a substituent and represented by the general formula (2).

Another exemplary embodiment of a (meth)acrylate compound represented by the general formula (1) in the present invention can be a compound in which X and Y are —O—; $R_1$ and $R_2$ are each an alkyl group having 1 or 2 carbon atoms; and $Z_1$ and $Z_2$ are each an alkyl group having 1 or 2 carbon atoms, having a substituent and represented by the general formula (2).

Since if the number of the branch points becomes large, the molecular weight of the compound inevitably increases and the optical property resultantly does not fall in the B region in FIG. 1, V in the general formula (2) is desirable. Although also the introduction of the branch structure to $R_1$ and $R_2$ in the general formula (1) can be anticipated to have a similar birefringence-reduction effect, the compound has a very high molecular rigidity, and even the introduction of the branch structure in the axis direction of the compound exhibits only a small effect on reduction of the birefringence. Conversely, since a few branch points may promote the orientation of the compound, the introduction of the branch structure represented by the general formula (2) to $Z_1$ and $Z_2$ is effective on reduction of the birefringence of a molded article prepared by molding the optical composition.

Then, one example of a method for manufacturing a (meth) acrylate compound represented by the general formula (1) in the present invention will be cited and described. The manufacture route of the (meth)acrylate compound according to the present invention is not especially limited, and any manufacture method can be employed. However, the manufacture method includes at least the following synthesis steps of (a), (b) and (c).

(a) A reaction for forming bonds between aromatic rings (benzene rings)
(b) An etherification (thioetherification) reaction
(c) A (meth)acrylation reaction In consideration of the easiness of synthesis and the like, the above synthesis steps are carried out in the order of (a), (b) and (c).

In the synthesis step (a), the reaction can be altered depending on the kind of a functional group of an aromatic compound. For example, the reaction is a coupling reaction using a transition metal catalyst, an oxidative coupling reaction of halides or a substitution reaction on an aromatic ring. Here, a coupling reaction using a transition metal catalyst is desirable in consideration of the yield of the reaction.

The coupling reaction using a transition metal catalyst can be selected optionally. A typical method to be suitably used is the Suzuki coupling utilizing boric acid or the like, the Stille coupling utilizing an organotin, the Negishi coupling utilizing an organozinc, or the like.

In the synthesis step (b), a typical method of an etherification reaction is the Williamson ether synthesis method in which after a hydroxy group is converted to a salt by sodium hydride, potassium hydroxide or the like, a corresponding halide is added, or the like.

On the other hand, the thioetherification reaction is carried out through a thiol group-forming reaction and a reaction of a thiol group and a halide. Here, the thiol group-forming reaction can be achieved, for example, by converting a hydroxy group to a substituent (TsO—, Cl—, $CF_3S(=O)_2$—O— or the like) having an activity to the nucleophilic substitution reaction, and thereafter carrying out the nucleophilic substitution reaction using sulfide ions ($S^{2-}$). To the reaction of a thiol group and a halide, the above-mentioned Williamson ether synthesis method or the like can be applied.

In the synthesis step (c), a typical method to be suitably used is a method of esterifying a hydroxy group using a (meth)acrylic acid halide or a (meth)acrylic anhydride, a transesterification reaction using a lower alcohol ester of (meth)acrylic acid, a direct esterification reaction in which (meth)acrylic acid and the diol are subjected to a dehydration condensation using a dehydration condensation agent such as N,N'-dicyclohexylcarbodiimide, a method in which (meth) acrylic acid and the diol are heated in the presence of a dehydration agent such as sulfuric acid, or the like.

A polymerization inhibitor may be used, as required, so that the polymerization does not proceed during the reaction and storage. Examples of the polymerization inhibitor include hydroquinones such as p-benzoquinone, hydroquinone, hydroquinone monomethyl ether and 2,5-diphenylparabenzoquinone, N-oxy radicals such as tetramethylpiperidinyl-N-oxy radical (TEMPO), substituted catechols such as t-butylcatechol, amines such as phenothiazine, diphenylamine and phenyl-β-naphthylamine, nitrosobenzene, picric acid, molecular oxygen, sulfur, and copper(II) chloride. Above all, hydroquinones, phenothiazine and N-oxy radicals are preferable from the viewpoint of the versatility and the polymerization retardation.

The amount of a polymerization inhibitor used, as its lower limit, is usually 10 ppm and can be 50 ppm, and as its upper limit, is usually 10,000 ppm and can be 5,000 ppm, based on the (meth)acrylate compound. The case where the amount is too small develops no or only a small effect as the polymerization inhibitor, and has a risk of the polymerization progressing in the reaction time and the concentration time in post-treatment steps; and the case where the amount is too large, for example, makes the polymerization inhibitor become an impurity in the manufacture time of a molded article described later, and has a risk of giving adverse effects such as the inhibition of the polymerization reactivity, which are therefore not preferable.

Then, features of a molded article prepared by molding an optical composition containing the (meth)acrylate compound represented at least by the above general formula (1) according to the present invention and a polymerization initiator will be described.

The present inventors have paid attention to that in order to impart a higher chromatic aberration correction function than conventionally to an optical element, satisfaction of the following (i) to (iii) as the material property of an optical element is very effective on the optical design.

(i) The transmittance in the visible light region is high.
(ii) The secondary dispersion property (θg,F) is out of general-purpose materials, and is higher (high θg,F property).
(iii) The birefringence is lower than 0.001.

Specifically, the 500 μm internal transmittance at 410 nm is 90% or more. Specifically, the relationship between the Abbe number ($v_d$) and the secondary dispersion property (θg,F) illustrated in FIG. 1 lies in the B area deviating from plots of glass materials and general-purpose materials of organic resins. Here, the property of the B area is $v_d$<25 and θg,F>0.70. Specifically, the birefringence in the visible light region is lower than 0.001.

As a result of exhaustive studies on materials satisfying the property of the B area illustrated in FIG. 1, the present inventors have found that an aromatic compound having a long conjugate structure having at least one conjugatable electron attracting substituent and electron releasing substituent each becomes a material unitedly having a high dispersion property (Abbe number ($v_d$)) and a high secondary dispersion property (θg,F) (high θg,F property) of the refractive index and a high property of chromatic aberration correction function, and the practicability. It has been also found that the introduction of branch structures on not positions in the axial direction of a compound but on positions deviated from the axial direction has an effect of reducing the birefringence. That is, the present inventors have found a compound having as a base structure a moiety structure represented by the following general formula (1) and general formula (2).

Formula 5

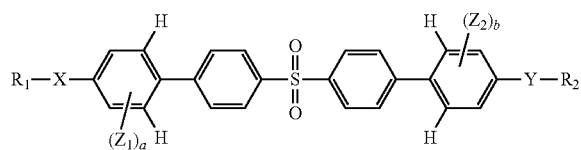

(1)

Formula 6

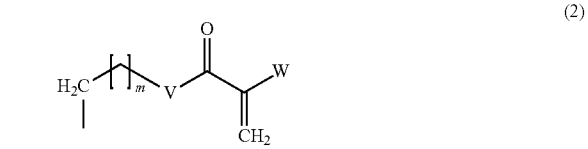

(2)

Since a compound having a long conjugate structure represented by an aromatic compound generally has a smaller band gap than general-purpose materials, the absorption edge of the ultraviolet region shifts to the visible light region side. The influence results in giving a high refractive index property to the compound having a long conjugate structure. Since the high refractive index property has a large influence on a shorter wavelength side, the secondary dispersion property (θg,F) inevitably becomes high, and the property of the compound falls in the B area illustrated in FIG. 1. However, only the construction of a long conjugate structure by simply linking aromatic compounds cannot provide a practicable material. For example, a large aromatic compound has a remaining problem in points of the synthesizability, the compatibility with other compounds and the coloration. Therefore, an aromatic compound having a long conjugate structure having at least one conjugatable electron attracting substituent and electron releasing substituent each is desirable.

From the viewpoint of making high the refractive index property and the secondary dispersion property, a longer conjugate length of the compound is thus better. However, since a too long conjugate structure decreases the transmittance on the short wavelength side in the visible light region, in the case of considering applications to optical materials, the length of the conjugate structure needs to be adjusted. Here, the moiety structure represented by the general formula (1) has such a conjugate length that the transmittance and the refractive index property are good.

Common methods of reducing the birefringence of a compound are a method in which a branch structure is introduced to the compound in order to destroy the molecular orientation to thereby make the moiety bulky, and a method in which benzene rings are made to be molecular-structurally orthogonal as in fluorene. However, only the simple introduction of a branch structure and a bulky structure to molecules cannot provide an anticipated effect of reducing the birefringence in some cases. Here, the introduction of the moiety structure represented by the general formula (2) as $Z_1$ and $Z_2$ in the general formula (1) effectively destroys the molecular orientation, and acts to reduce the birefringence.

Here, the conjugatable electron attracting substituent includes sulfone, ketone, imine, oxime, nitrile, nitro and ester. In consideration of the long-term stability of the product, the substituent can be sulfone, ketone, nitrile or ester, and is more preferably sulfone. Therefore, a molded article prepared by molding the optical composition according to the present invention contains at least a compound having a sulfone skeleton as represented by the general formula (1).

The conjugatable electron releasing substituent includes a hydroxyl group, a mercapto group, an alkoxy group, an alkylthio group, an alkyl group, an amino group, an alkylamino group, a dialkylamino group and a carbonyloxy group. The substituent can be a hydroxyl group, a mercapto group, an alkoxy group, an alkylthio group, an alkyl group and a carbonyloxy group. Provided that a too high molecular weight of the substituent cannot provide a high secondary dispersion property (θg,F). Therefore, the substituent is desirably a substituent having 0 to 10 carbon atoms. The substituent can be a substituent having 1 or 2 carbon atoms from the viewpoint of easiness of the synthesis. In the present invention, as especially preferable substituents, a hydroxyl group, a mercapto group, an alkoxy group having 1 or 2 carbon atoms and an alkylthio group having 1 or 2 carbon atoms are selected.

H (hydrogen atom) indicated in the general formula (1) is necessary for adjusting the conjugate structure, and the case of other substituents causes breaking of the conjugation due to twisting between aromatic rings caused by the steric hindrance of the substituents not to thereby develop the property in some cases.

Then, the molded article according to the present invention will be described.

The molded article according to the present invention is characterized by being prepared by molding a polymer of the above-mentioned optical composition.

The molded article according to the present invention is roughly classified in the following (A) to (C).

(A) A molded article prepared by polymerizing the (meth)acrylate compound according to the present invention.

(B) A molded article prepared by copolymerizing the (meth)acrylate compound according to the present invention with another compound.

(C) A molded article prepared by dispersing the (meth)acrylate compound according to the present invention in a matrix polymer.

Here, among the (meth)acrylate compounds according to the present invention, compounds having no (meth)acryloyl group are used in the form of (C). By contrast, among the (meth)acrylate compounds according to the present invention, compounds having a (meth)acryloyl group can be used in the any form of (A) to (C), but are exclusively used in the form of (A) or (B).

In the case of using the (meth)acrylate compound according to the present invention in the form of (A), the molded article according to the present invention is fabricated of an optical composition containing the (meth)acrylate compound according to the present invention and a polymerization initiator. Here, to the optical composition, as required, a polymerization inhibitor, a photosensitizer, a light-resistive stabilizer, a heat-resistive stabilizer, an antioxidant and the like may further be incorporated.

The polymerization initiator includes polymerization initiators generating radical species or cationic species by light irradiation, and polymerization initiators generating radical species by heat, but is not especially limited thereto.

The polymerization initiator generating a radical species by light irradiation includes 2-benzyl-2-dimethylamino-1-(4-morpholinophenyl)-1-butanone, 1-hydroxy-cyclohexyl-phenyl ketone, 2-hydroxy-2-methyl-1-phenyl-propan-1-one, bis (2,4,6-trimethylbenzoyl)-phenylphosphine oxide, 4-phenylbenzophenone, 4-phenoxybenzophenone, 4,4'-diphenylbenzophenone and 4,4'-diphenoxybenzophenone, but is not limited thereto.

The suitable polymerization initiator generating a cationic species by light irradiation includes iodonium (4-methylphenyl)[4-(2-methylpropyl)phenyl]-hexafluorophosphate, but is not limited thereto.

The polymerization initiator generating a radical species by heat includes azo compounds such as azobisisobutyronitrile (AIBN), and peroxides such as benzoyl peroxide, t-butyl peroxypivalate, t-butyl peroxyneohexanoate, t-hexyl peroxyneohexanoate, t-butyl peroxyneodecanoate, t-hexyl peroxyneodecanoate, cumyl peroxyneohexanoate, and cumyl peroxyneodecanoate, but is not limited thereto.

The polymerization inhibitor includes methoquinones such as 4-methoxyphenol and phenols such as (3,5-di-tert-butyl-4-hydroxyphenyl)propionate, but is not limited thereto. However, hydroquinones such as hydroquinone and benzoquinones such as benzoquinone are not suitable because these sometimes turn yellow by UV irradiation.

The polymerization inhibitor includes the above-mentioned compounds as polymerization retarders in the reaction time and the storage time, but is not limited thereto. The amount added can be in the range of 0.01% by mass or more and 1.00% by mass or less of the optical composition.

The photosensitizer includes benzophenone, 4,4-diethylaminobenzophenone, 1-hydroxycyclohexyl phenyl ketone, isoamyl p-dimethylaminobenzoate, methyl 4-dimethylaminobenzoate, benzoin, benzoin ethyl ether, benzoin isobutyl ether, benzoin isopropyl ether, 2,2-diethoxyacetophenone, methyl o-benzoylbenzoate, 2-hydroxy-2-methyl-1-phenylpropan-1-one and acylphosphine oxide, but is not limited thereto.

The light-resistive stabilizer is not especially limited as long as not having a large effect on the optical property of a molded article, and is a benzotriazol-based material such as 2-(2H-benzotriazol-2-yl)-p-cresol, 2-(2H-benzotriazol-2-yl)-4,6-bis(1-methyl-1-phenylethyl)phenol, 2-[5-chloro(2H)-benzotriazol-2-yl]-4-methyl-6-(tert-butyl)phenol, 2-(2H-benzotriazol-2-yl)-4,6-di-tert-pentylphenol, 2-(2H-benzotriazol-2-yl)-4-(1,1,3,3-tetramethylbutyl)phenol, 2,2'-methylenebis[6-(2H-benzotriazol-2-yl)-4-(1,1,3,3-tetramethylbutyl)phenol or 2-(2H-benzotriazol-2-yl)-6-dodecyl-4-methylphenol, cyanoacrylate-based materials such as ethyl 2-cyano-3,3-diphenylacrylate or 2-ethylhexyl 2-cyano-3,3-diphenylacrylate, a triazine-based material, a benzophenone-based material such as octabenzone or 2,2'-4,4'-tetrahydrobenzophenone, or the like.

The heat-resistive stabilizer is not especially limited as long as not having a large effect on the optical property of a molded article, and is a hindered phenolic material such as pentaerythritol tetrakis[3-(3,5-di-tert-butyl-4-hydroxyphenyl)propionate, octadecyl-3-(3,5-di-tert-butyl-4-hydroxyphenyl) propionate, benzenepropanoic acid, 3,5-bis(1,1-dimethylethyl)-4-hydroxy-, C7-C9-branched alkyl esters, 4,6-bis(octylthiomethyl)-o-cresol, 4,6-bis(dodecylthiomethyl)-o-cresol, ethylene bis(oxyethylene)bis[3-(5-tert-butyl-4-hydroxy-m-tolyl)propionate or hexamethylene bis[3-(3,5-di-tert-butyl-4-hydroxyphenyl) propionate, a phosphorus-based material such as tris(2,4-di-tert-butylphenyl)phosphite, a sulfur-based material such as dioctadecyl 3,3'-thiodipropionate, or the like.

The antioxidant is not especially limited as long as not having a large effect on the optical property of a molded article, and is a hindered amine-based material such as bis(2,2,6,6-tetramethyl-4-piperidyl)sebacate, bis(1,2,2,6,6-pentamethyl-4-piperidyl)[[3,5-bis(1,1-dimethylethyl)-4-hydroxyphenyl]methyl]butyl malonate, or the like.

In the case of using the (meth)acrylate compound according to the present invention in the form of (B) in the molded article according to the present invention, the content of the (meth)acrylate compound according to the present invention is desirably 1.0% by mass or more and 99% by mass or less, and can be 50% by mass or more and 99% by mass or less.

The molded article according to the present invention is fabricated of an optical composition including the (meth)acrylate compound according to the present invention and a material copolymerizable with the (meth)acrylate compound according to the present invention. To the optical composition, as required, a polymerization inhibitor, a photosensitizer, a light-resistive stabilizer, a heat-resistive stabilizer, an antioxidant and the like may further be incorporated.

The copolymerizable material includes, for example, (meth)acrylic monomers, but is not especially limited. Examples thereof include (meth)acrylate compounds such as 1,3-adamantanediol dimethacrylate, 1,3-adamantanedimethanol dimethacrylate, tricyclodecanedimethanol diacrylate, pentaerythritol tetraacrylate, propoxylated neopentylglycol diacrylate, dipropylene glycol diacrylate, ethoxylated bisphenol A dimethacrylate, tris(2-hydroxyethyl)isocyanurate triacrylate, 2(2-ethoxyethoxy)ethyl acrylate, stearyl acrylate, tetrahydrofurfuryl acrylate, 2-phenoxyethyl acrylate, isodecyl acrylate, isobonyl acrylate, isobonyl methacrylate, 1,3-butylene glycol diacrylate, 1,4-butanediol diacrylate, diethylene glycol diacrylate, 1,6-hexanediol diacrylate, triethylene glycol diacrylate, tripropylene glycol diacrylate, dipropylene glycol diacrylate, triethylene glycol dimethacrylate, ethylene glycol dimethacrylate, tetraethylene glycol dimethacrylate, 1,4-butanediol dimethacrylate, diethylene glycol dimethacrylate, 1,6-hexanediol dimethacrylate, tripropylene glycol dimethacrylate, dipropylene glycol dimethacrylate, trimethylolpropane trimethacrylate, 9,9-bis[4-(2-acryloyloxyethoxy)phenyl]fluorene, 9,9-bis[4-(2-methacryloyloxyethoxy)phenyl]fluorene, 9,9-bis[4-(2-acryloyloxy)phenyl]fluorene, 9,9-bis[4-(2-methacryloyloxy)phenyl]fluorene, benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol diacrylate, polyethylene glycol dimethacrylate, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxyphenyl)propane, 2,2-bis(4-methacryloxyethoxyphenyl)propane, 2,2-bis(4-acryloxydiethoxyphenyl)propane, 2,2-bis(4-methacryloxydiethoxyphenyl)propane, bisphenol F diacrylate, bisphenol F dimethacrylate, 1,1-bis(4-acryloxyethoxyphenyl)methane, 1,1-bis(4-methacryloxyethoxyphenyl)methane, 1,1-bis(4-acryloxydiethoxyphenyl)methane, 1,1-bis(4-methacryloxydiethoxyphenyl)methane, 1,1-bis(4-acryloxyethoxyphenyl)sulfone, 1,1-bis(4-methacryloxyethoxyphenyl)sulfone, 1,1-bis(4-acryloxydiethoxyphenyl)sulfone, 1,1-bis(4-methacryloxydiethoxyphenyl)sulfone, dimethyloltricyclodecane diacrylate, trimethylolpropane triacrylate, trimethylolpropane trimethacrylate, glycerol diacrylate, glycerol dimethacrylate, pentaerythritol triacrylate, pentaerythritol tetraacrylate, pentaerythritol tetramethacrylate, methyl thioacrylate, methyl thiomethacrylate, phenyl thioacrylate, benzyl thiomethacrylate, xylylene dithiol diacrylate, xylylene dithiol dimethacrylate, mercaptoethyl sulfide diacrylate and mercaptoethyl sulfide dimethacrylate, allyl compounds such as allyl glycidyl ether, diallyl phthalate, diallyl terephthalate, diallyl isophthalate, diallyl carbonate and diethylene glycol bisallyl carbonate, vinyl compounds such as styrene, chlorostyrene, methylstyrene, bromostyrene, dibromostyrene, divinylbenzene and 3,9-divinylspirobi(m-dioxane), and diisopropenylbenzene. However, the present invention is not limited thereto.

The amount of the copolymerizable material added can be in the range of 0.1% by mass or more and 80.00% by mass or less of the optical composition. In consideration of the $\theta g, F$ and transmittance properties of an obtained molded article, the amount can be 0.1% by mass or more and 30.0% by mass or less.

The amount of a polymerization initiator added to be contained in the optical composition according to the present invention can be in the range of 0.01% by mass or more and 10.00% by mass or less with respect to a polymerizable component. The polymerization initiator, depending on the reactivity of a resin and the wavelength of light irradiation, may be used in only one kind of the above-mentioned polymerization initiators, or may be used concurrently in two or more thereof. The addition ratio of a polymerization initiator to a polymerizable resin component can suitably be selected according to the amount of light irradiation and additionally the heating temperature. The ratio can also be adjusted according to an aimed average molecular weight of an obtained polymer.

A polymerization inhibitor contained in the optical composition according to the present invention includes the above-mentioned polymerization inhibitors. The amount added can be in the range of 0.01% by mass or more and 10.00% by mass or less of the optical composition.

In the case of initiating the polymerization by irradiation of ultraviolet rays or the like as light, a well-known sensitizer or the like may be used. Typical photosensitizers are as described above. The amount of a photosensitizer added to be contained in the optical composition according to the present invention can be in the range of 0.01% by mass or more and 10.00% by mass or less of the optical composition.

A light-resistive stabilizer contained in the optical composition according to the present invention includes the above-mentioned light-resistive stabilizers. The amount added can be in the range of 0.01% by mass or more and 10.00% by mass or less of the optical composition.

A heat-resistive stabilizer contained in the optical composition according to the present invention includes the above-mentioned heat-resistive stabilizers. The amount added can be in the range of 0.01% by mass or more and 10.00% by mass or less of the optical composition.

An antioxidant contained in the optical composition according to the present invention includes the above-mentioned antioxidants. The amount added can be in the range of 0.01% by mass or more and 10.00% by mass or less of the optical composition.

In the case of using the (meth)acrylate compound according to the present invention in the form of (C) in the molded article according to the present invention, the content of the (meth)acrylate compound contained in the optical composition according to the present invention is desirably 1.0% by mass or more and 99% by mass or less, and in consideration of the θg,F, transmittance and birefringence of an obtained molded article, and the compatibility of the (meth)acrylate compound according to the present invention with a matrix polymer, the content can be 1.0% by mass or more and 50% by mass or less.

The molded article according to the present invention is fabricated of an optical composition including the (meth) acrylate compound according to the present invention and a matrix polymer. Here, to the optical composition, as required, a polymerization inhibitor, a photosensitizer, a light-resistive stabilizer, a heat-resistive stabilizer, an antioxidant and the like may further be incorporated.

The matrix polymer includes (meth)acrylic polymers; allylic polymers; polyolefinic resins including ethylene homopolymers, random or block copolymers of ethylene with one or two or more α-olefins such as propylene, 1-butene, 1-pentene, 1-hexene and 4-methyl-1-pentene, random or block copolymers of ethylene with one or two or more of vinyl acetate, acrylic acid, methacrylic acid, methyl acrylate and methyl methacrylate, propylene homopolymers, random or block copolymers of propylene with one or two or more α-olefins except propylene such as 1-butene, 1-pentene, 1-hexene and 4-methyl-1-pentene, 1-butene homopolymers, ionomer resins, and mixtures of these polymers; hydrocarbon-based resins such as petroleum resins and terpene resins; polyesteric resins such as polyethylene terephthalate, polybutylene terephthalate and polyethylene naphthalate; polyamide-based resins such as nylon 6, nylon 66, nylon 11, nylon 12, nylon 610, nylon 6/66, nylon 66/610 and nylon MXD; acrylic resins such as polymethyl methacrylate; styrenic or acrylonitrile-based resins such as polystyrene, styrene-acrylonitrile copolymers, styrene-acrylonitrile-butadiene copolymers and polyacrylonitrile; polyvinyl alcoholic resins such as polyvinyl alcohol and ethylene-vinyl alcohol copolymers; polycarbonate resins; polyketone resins; polymethylene oxide resins; polysulfone resins; polyimide resins; and polyamide-imide resins, but is not limited thereto. These resins may be used singly or as a mixture of two or more. These matrix polymers are suitably selected in consideration of the compatibility with an organic compound for the optical material according to the present invention.

Then, the optical element according to the present invention will be described by reference to the drawing.

Figure 2A:
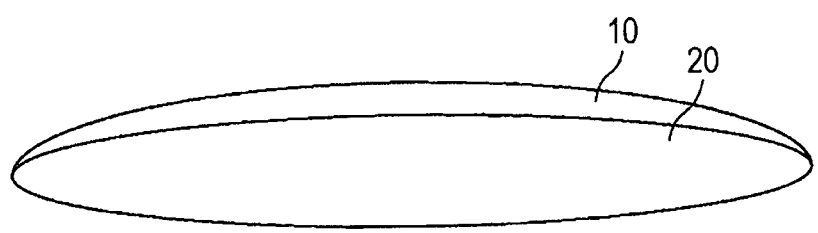
FIGS. 2A and 2B are schematic diagrams illustrating examples of the optical element according to the present invention.
Figure 2B:
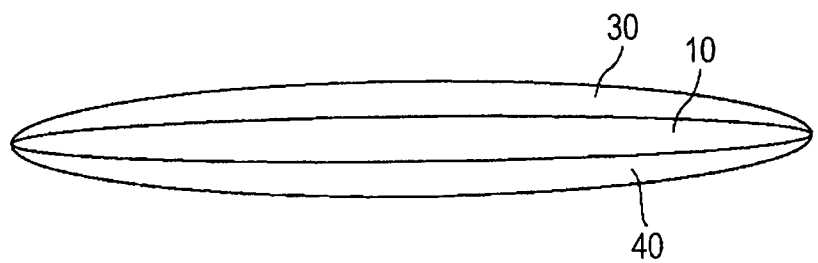

The optical element according to the present invention is characterized by having the above-mentioned molded article. In the present description, the optical element includes a mirror, a lens, a prism and a filter. The optical element according to the present invention can be used for a lens. FIGS. 2A and 2B are schematic diagrams illustrating an example of the optical element according to the present invention. An optical element of FIG. 2A is configured such that a thin film (optical member 10) prepared by molding and processing the optical composition is provided on one surface of a lens substrate 20. A method to be employed for fabricating the optical element of FIG. 2A is, for example, a method of forming a thin-layer structure on a substrate including a light-transmissive material. Specifically, a die including a metal material is provided at a certain distance from a glass substrate, and a fluid optical composition is filled in a gap between the die and the glass substrate, which are then slightly pressed to thereby carry out molding. Then as required, the optical composition is polymerized in the pressed state maintained. The light irradiation provided for the polymerization reaction is carried out using light of a suitable wavelength, usually ultraviolet light or visible light, corresponding to a mechanism causing radical formation using a photopolymerization initiator. For example, the light irradiation is carried out uniformly on the raw material including a monomer of the molded optical composition through a light-transmissive material utilized as the substrate, specifically a glass substrate. The amount of irradiation light is suitably selected according to the mechanism causing the radical formation utilizing the photopolymerization initiator and also according to the content ratio of the contained photopolymerization initiator.

On the other hand, in the fabrication of a molded article of the optical composition by the photopolymerization reaction, the irradiation light is more preferably irradiated uniformly on the entire of the raw material including a monomer molded. Therefore, in the light irradiation to be utilized, it is more preferable that light of a wavelength capable of uniformly carrying out the irradiation through a light-transmissive material utilized as the substrate, specifically a glass substrate, is selected. At this time, making thin the thickness of a molded article of an optical material formed on a substrate of a light-transmissive material is more suitable for the present invention.

On the other hand, an optical element of FIG. 2B is configured such that a thin film (optical member 10) prepared by molding and processing the optical composition is provided between a lens substrate 30 and a lens substrate 40. A method for fabricating the optical element of FIG. 2B involves, for example, pouring a similar uncured resin composition and the like between both of the surface of the optical composition of the above-mentioned molded article and an another corresponding lens, which are then slightly pressed to thereby carry out molding. Then, the uncured resin composition is photopolymerized in the pressed state maintained. A molded article in which the optical composition is interposed between the lenses can be thereby obtained.

A molded article can similarly be fabricated by a thermopolymerization method. In this case, the more uniformization of the temperature of the entire is desirable, and making small the total thickness of a molded article of a polymerizable composition formed on a substrate of a light-transmissive material is more suitable for the present invention. In the case of making large the total thickness of a molded article of an optical composition to be formed, the amount of irradiation, the irradiation intensity, the light source and the like need to be selected in more consideration of the layer thickness, the absorption of resin components and the absorption of microparticulate components.

On the other hand, in the case of using the (meth)acrylate compound according to the present invention in the above-mentioned form of (C), a method for molding an optical composition is not especially limited, but is especially preferably melt molding in order to obtain a molded product excellent in properties such as the low double refraction, the mechanical strength and the dimensional accuracy. The melt molding method includes pressing, extrusion and injection molding, but the injection molding is preferable from the viewpoint of the moldability and the productivity.

The molding condition in the molding step is suitably selected according to the usage purpose or the molding method; but the temperature of a resin composition in the injection molding can be in the range of 150° C. to 400° C., and is more preferably in the range of 200° C. to 350° C., and especially preferably in the range of 200° C. to 330° C. Molding in the temperature range can impart a reasonable fluidity to a resin in the molding time and prevent the generation of sink marks and distortions of a molded article, prevent the generation of silver streaks due to thermal decomposition of the resin, and can further prevent effectively yellowing of a molded product.

A molded article prepared by molding the optical composition according to the present invention by the above-mentioned molding method can be used as an optical element. Utility examples of the optical element include camera lenses.

Hereinafter, the present invention will be described in more detail by way of Examples, but is not limited to Examples described below unless departing from its gist. The abbreviations in reaction formulae are as follows. The analysis of molecular structures of synthesized compounds was carried out using JNM-ECA400 NMR, made by JEOL Ltd.

THF: tetrahydrofuran
DMF: N,N-dimethylformamide
TsOH: para-toluenesulfonic acid hydrate Synthesis Example 1

Synthesis of 4,4'-bis(4-hydroxyphenyl)diphenyl sulfone

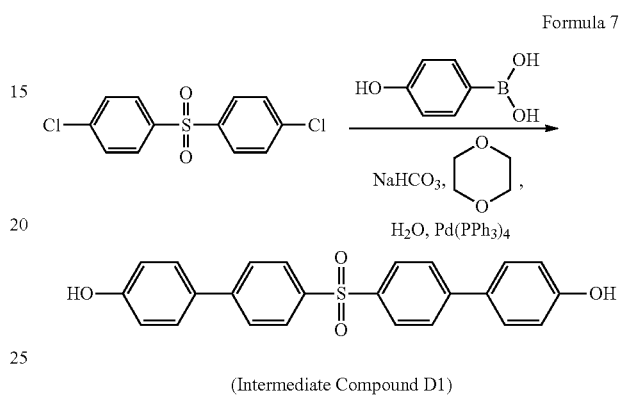

(Intermediate Compound D1)

Reagents and solvents described below were charged in a reaction vessel.
4,4'-Dichlorodiphenyl sulfone: 15 g
4-Hydroxyphenylboronic acid: 21 g
Sodium hydrogencarbonate: 33 g
1,4-Dioxane: 500 ml
Water: 250 ml
Tetrakistriphenylphosphine palladium: 2.5 g Then, the reaction solution was heated to 90° C., and stirred at this temperature (90° C.) for 20 hours. At this time, the degree of the reaction progress was checked on occasion by thin-layer chromatography (hereinafter, TLC). After the completion of the reaction, the reaction solution was diluted with water, and thereafter, an organic phase was recovered by solvent extraction. Then, the organic layer was washed with water and saturated brine in order, and thereafter dried with anhydrous magnesium sulfate. Then, the organic phase was concentrated under reduced pressure to thereby obtain a residue, which was then subjected to recrystallization refining with a mixed solution of hexane and ethyl acetate to thereby obtain 20 g (yield: 95%) of a light yellow crystal, 4,4'-bis(4-hydroxyphenyl)diphenyl sulfone (hereinafter, referred to as an intermediate compound D1).

Synthesis Example 2

Synthesis of 4,4'-bis(3-hydroxymethyl-4-methoxyphenyl)diphenyl sulfone

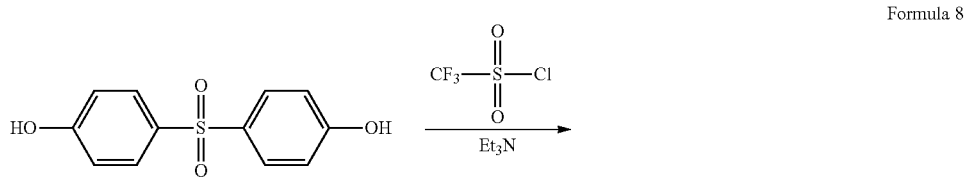

-continued

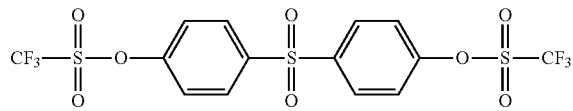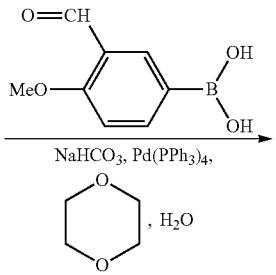

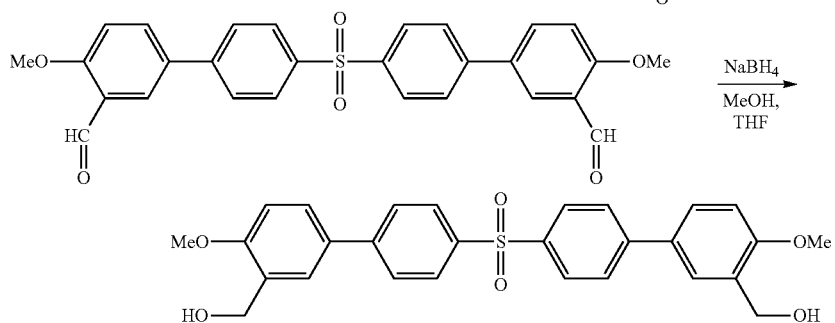

(Intermediate Compound D2)

(1) Reagents and a solvent described below were charged in a reaction vessel.
4,4'-Dihydroxydiphenyl sulfone: 25 g
Trifluoromethanesulfonyl chloride: 25 ml
Chloroform: 300 ml Then, the reaction solution was cooled to 0° C., and thereafter, 42 ml of triethylamine was slowly dropwise charged. Then, the reaction solution was stirred at the same temperature (0° C.) for 1 hour. Then, the reaction solution was heated to room temperature, and further stirred for 5 hours. At this time, the degree of the reaction progress was checked on occasion by TLC. Then, the reaction was suspended with an ammonium chloride aqueous solution, and an organic phase was extracted with ethyl acetate. Then, the obtained organic phase was washed with water and saturated brine in order, and thereafter dried with anhydrous magnesium sulfate. Then, the organic phase was concentrated under reduced pressure to thereby obtain a crude product, which was then subjected to recrystallization refining with a hexane/ethyl acetate mixed solvent to thereby obtain 49 g (yield: 94%) of diphenylsulfone-4,4'-diylbis(trifluoromethanesulfonate). The compound thus obtained here was used as it was in the following step.

(2) Reagents and solvents described below were charged in a reaction vessel.
Diphenylsulfone-4,4'-diylbis(trifluoromethanesulfonate) (which was synthesized in (1) and used as it was): 28 g
3-Formyl-4-methoxyphenylboric acid: 25 g
Sodium hydrogencarbonate: 30 g
Tetrakistriphenylphosphine palladium: 1.3 g
1,4-Dioxane: 500 ml
Water: 250 ml Then, the reaction solution was heated to 80° C., and stirred at this temperature (80° C.) for 3 hours. At this time, the degree of the reaction progress was checked on occasion by TCL. Then, 250 ml of water was added, and thereafter, the reaction solution was stirred at 80° C. for 1 hour. Then, a produced crystal (crude crystal) was filtered and recovered, and thereafter, the crude crystal was washed with ethanol, and then subjected to recrystallization refining with a hexane/ethyl acetate mixed solvent to thereby obtain a light gray crystal.

Then, the obtained light gray crystal and solvents described below were charged in a reaction vessel.
Methanol: 200 ml
Tetrahydrofuran: 200 ml Then, the reaction solution was cooled to 0° C., and thereafter, 12 g of sodium borohydride was slowly added. Then, while the degree of the reaction progress was checked by TLC, the reaction solution was stirred at the same temperature (0° C.). After confirmation of the progress of the reaction, a 2N hydrochloric acid aqueous solution was added. Then, the reaction solution was stirred at room temperature for 1 hour. Then, a produced crystal was washed with a sodium hydrogencarbonate aqueous solution and water in order. Then, the crystal was subjected to recrystallization refining with an ethanol/ethyl acetate/hexane mixed solvent to thereby obtain 48 g (yield: 90%) of 4,4'-bis(3-hydroxymethyl-4-methoxyphenyl)diphenyl sulfone (hereinafter, referred to as an intermediate compound D2).

Synthesis Example 3

Synthesis of 4,4'-bis(3-bromomethyl-4-methoxyphenyl)diphenyl sulfone

Formula 9

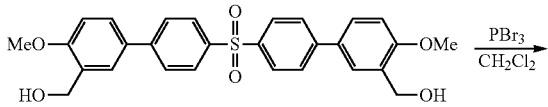

-continued

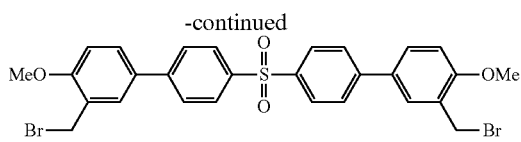

(Intermediate Compound D3)

A reagent and a solvent described below were charged in a reaction vessel.

The intermediate compound D2 synthsized in Synthesis Example 2: 361 g
Dichloromethane: 14 L Then, the reaction vessel was cooled to 0° C., and 169 g of phosphorus tribromide was slowly dropwise charged; and after the completion of the dropwise charging, the mixture was stirred for 3 hours while the temperature was being raised to 20° C.

Then, the reaction liquid was poured under stirring in 14 L of water at 10° C. or less and kept to be stirred for 0.5 hour, and the reaction was suspended. An organic phase only was extracted from the mixed liquid of the organic phase and a water phase, and dried up by removing the solvent by an evaporator. 5.0 L of THF was added thereto to disperse the dried-up crystal, and the rotation of the evaporator was continued for 15 min under no reduced pressure.

Then, the THF dispersion liquid was poured under stirring in a vessel containing 15 L of water to thereby precipitate the crystal. The precipitated crystal was filtered, and washed with water until the filtrate became neutral. Thereafter, the obtained crystal was washed with 2.0 L of methanol. The obtained crystal was dried for 24 hours by air blowing, and thereafter dried for 24 hours by hot air of 70° C. to thereby obtain 410 g (yield: 90%) of 4,4'-bis(3-bromomethyl-4-methoxyphenyl)diphenyl sulfone (hereinafter, referred to as an intermediate compound D3).

Example 1

A synthesis scheme of a compound synthesized in Example 1 will be shown below. A specific synthesis method will be described below.

Formula 10

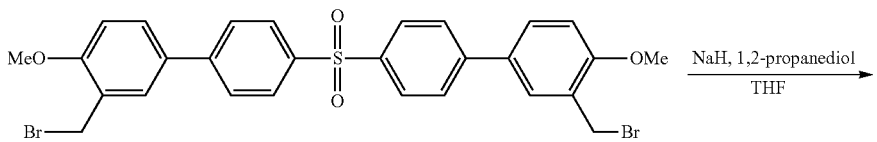

(Intermediate Compound D3)

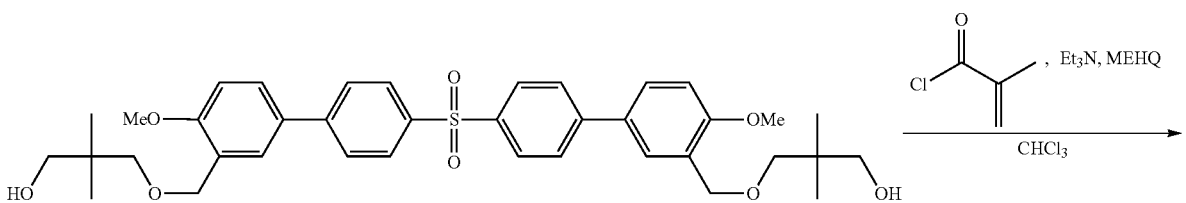

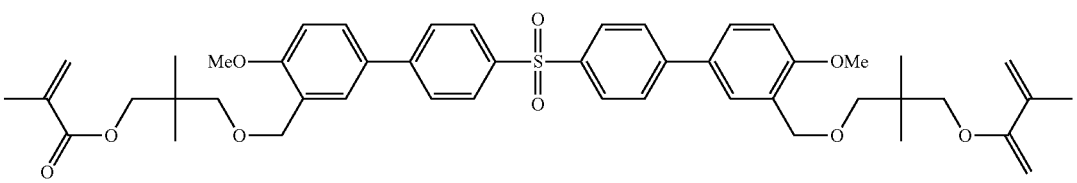

Here, the symbol of a cross of (—) and (|) at the position of —O—C$_2$H$_3$(CH$_3$)—O— in the formula of the above compound represents a mixture in which both CH$_3$ bonding to the right-side carbon atom and CH$_3$ bonding to the left-side carbon atom are present.

(1) A reagent and a solvent described below were charged in a reaction vessel.

Sodium hydride: 24
THF: 1.0 L

Then, the reaction vessel was cooled to 0° C., and a liquid of 150 g of 1,2-propanediol diluted with 0.5 L of THF was slowly dropwise charged. After the completion of the dropwise charging, the reaction vessel was heated to 20° C., and the mixture was stirred further for 1 hour. 100 g of the intermediate compound was added thereto at one time, and the reaction vessel was heated to 60° C. and the mixture was stirred for 5 hours. The reaction was suspended by water; an organic phase was extracted with ethyl acetate; thereafter, the obtained organic phase was washed with water and saturated brine in order, and dried with anhydrous magnesium sulfate. Then, the organic phase was concentrated under reduced pressure to thereby obtain a crude product. The obtained crude product was refined by silica gel chromatography to thereby obtain 88 g (yield: 70%) of a light yellow liquid.

(2) 5.0 g of the diol synthesized in (1) of the present Example, 20 ml of chloroform, 20 mg of MEHQ (4-methoxyphenol) and 10 ml of pyridine were charged in a reaction vessel. The reaction vessel was cooled to 0° C., and 2.5 ml of methacryloyl chloride was dropwise charged. The reaction liquid was diluted with 30 ml of toluene, and thereafter, the reaction was suspended by a 2N hydrochloric acid aqueous solution; and an obtained organic layer was washed with an acidic and basic aqueous solutions, and thereafter dried with saturated brine and anhydrous magnesium sulfate. A crude product obtained by removing the solvent was refined by silica gel chromatography to thereby obtain 2.8 g (yield: 56%) of 4,4'-bis((3-(2-methacryloyloxypropoxy)methyl)-4-methoxyphenyl)diphenyl sulfone.

Example 2

A synthesis scheme of a compound synthesized in Example 2 will be show below. A specific synthesis method will be described below.

Formula 11

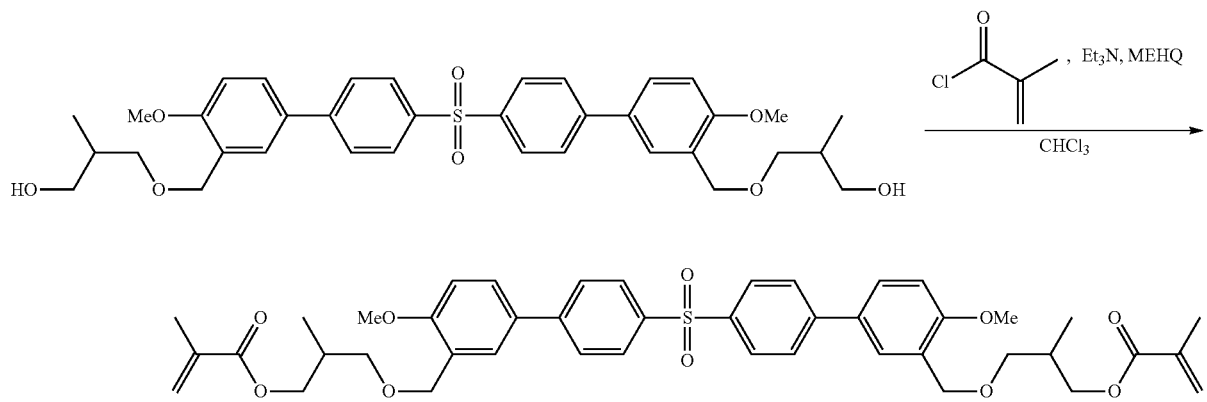

(1) A reagent and a solvent described below were charged in a reaction vessel.

Sodium hydride: 24 g
THF: 1.0 L

Then, the reaction vessel was cooled to 0° C., and a liquid of 144 g of 2-methyl-1,3-propanediol diluted with 0.5 L of THF was slowly dropwise charged. After the completion of the dropwise charging, the reaction vessel was heated to 20° C., and the mixture was stirred further for 1 hour. 100 g of the intermediate compound was added thereto at one time, and the reaction vessel was heated to 60° C. and the mixture was stirred for 5 hours. The reaction was suspended by water; an organic phase was extracted with ethyl acetate; thereafter, the obtained organic phase was washed with water and saturated brine in order, and dried with anhydrous magnesium sulfate. Then, the organic phase was concentrated under reduced pressure to thereby obtain a crude product. The obtained crude product was refined by silica gel chromatography to thereby obtain 88 g (yield: 70%) of a light yellow liquid.

(2) 5.0 g of the diol synthesized in (1) of the present Example, 20 ml of chloroform, 20 mg of MEHQ and 10 ml of pyridine were charged in a reaction vessel. The reaction vessel was cooled to 0° C., and 2.5 ml of methacryloyl chloride was dropwise charged. The reaction liquid was diluted with 30 ml of toluene, and thereafter, the reaction was suspended by a 2N hydrochloric acid aqueous solution; and an obtained organic layer was washed with an acidic and basic aqueous solutions, and thereafter dried with saturated brine and anhydrous magnesium sulfate. A crude product obtained by removing the solvent was refined by silica gel chromatography to thereby obtain 3.5 g (yield: 71%) of 4,4'-bis((3-(2-methacryloyloxy-2-methylpropoxy)methyl)-4-methoxyphenyl)diphenyl sulfone.

Example 3

A synthesis scheme of a compound synthesized in Example 3 will be show below. A specific synthesis method will be described below.

obtained organic phase was washed with water and saturated brine in order, and dried with anhydrous magnesium sulfate. Then, the organic phase was concentrated under reduced pressure to thereby obtain a crude product. The obtained crude product was refined by silica gel chromatography to thereby obtain 45 g (yield: 75%) of a light yellow liquid.

(2) 5.0 g of the diol synthesized in (1) of the present Example, 20 ml of chloroform, 20 mg of MEHQ and 10 ml of pyridine were charged in a reaction vessel. The reaction vessel was cooled to 0° C., and 2.5 ml of methacryloyl chloride was dropwise charged. The reaction liquid was diluted with 30 ml of toluene, and thereafter, the reaction was suspended by a 2N hydrochloric acid aqueous solution; and an obtained organic layer was washed with an acidic and basic aqueous

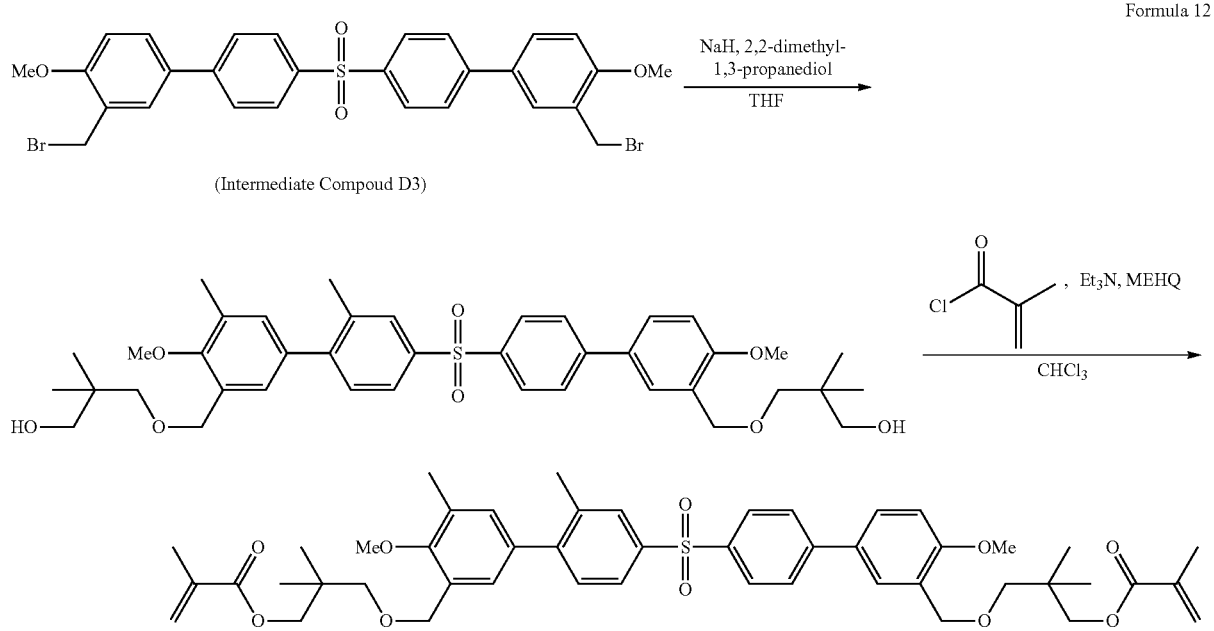

Formula 12

(Intermediate Compoud D3)

(1) A reagent and a solvent described below were charged in a reaction vessel.
  Sodium hydride: 12 g
  THF: 0.5 L
Then, the reaction vessel was cooled to 0° C., and a liquid of 70 g of 2,2-dimethyl-1,3-propanediol diluted with 0.2 L of THF was slowly dropwise charged. After the completion of the dropwise charging, the reaction vessel was heated to 20° C., and the mixture was stirred further for 1 hour. 50 g of the intermediate compound was added thereto at one time, and the reaction vessel was heated to 60° C. and the mixture was stirred for 5 hours. The reaction was suspended by water; an organic phase was extracted with ethyl acetate; thereafter, the solutions, and thereafter dried with saturated brine and anhydrous magnesium sulfate. A crude product obtained by removing the solvent was refined by silica gel chromatography to thereby obtain 2.9 g (yield: 49%) of 4,4'-bis((3-(3-methacryloyloxy-2,2-dimethylpropoxy)methyl)-4-methoxyphenyl)diphenyl sulfone.

Comparative Example 1

A synthesis scheme of a compound synthesized in
Comparative Example 1 will be show below. A specific synthesis method will be described below.

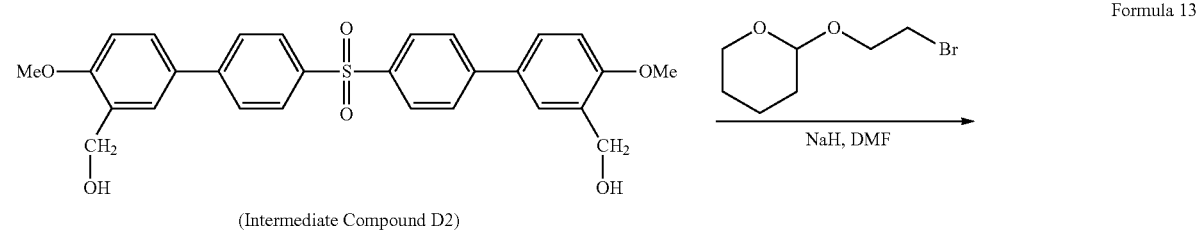

Formula 13

(Intermediate Compound D2)

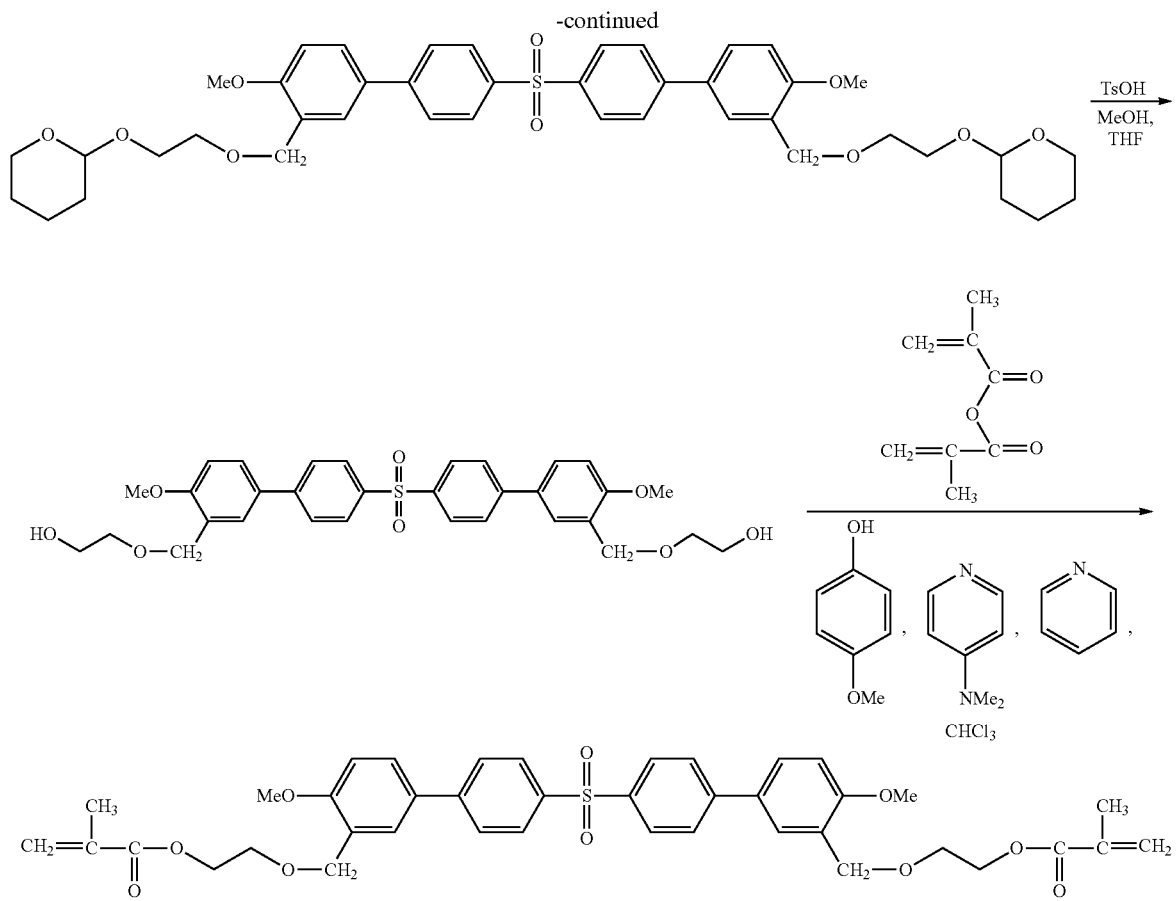

-continued (1) A reagent and a solvent described below were charged in a reaction vessel.
Sodium hydride (55%): 11 g
N,N-dimethylformamide: 300 ml Then, the reaction solution was cooled to 0° C., and thereafter, the intermediate compound D2 (30 g) was slowly added. Then, the reaction solution was stirred at the same temperature (0° C.) for 1 hour. Then, 36 ml of 2-(2-bromoethoxy)tetrahydro-2H-pyran was added, and thereafter, the reaction solution was heated to 70° C., and stirred at the temperature (70° C.) for 6 hours. At this time, the degree of the reaction progress was checked on occasion by TLC. Then, water was added to suspend the reaction, and thereafter, an organic layer was extracted with ethyl acetate. Then, the obtained organic layer was washed with water and saturated brine in order, and thereafter dried with anhydrous magnesium sulfate. Then, a crude product obtained by concentrating the organic layer under reduced pressure was refined by column chromatography to thereby obtain a light yellow liquid. The light yellow liquid thus obtained was used as it was in the following step.

(2) The light yellow liquid obtained in the above (1), a reagent and solvents described below were charged in a reaction vessel.
Methanol: 150 ml
Tetrahydrofuran: 50 ml
Para-toluenesulfonic acid: catalytic amount Then, the reaction solution was stirred at room temperature for 12 hours. At this time, the degree of the reaction progress was checked on occasion by TLC. Then, triethylamine was added to suspend the reaction, and a produced crystal was filtered and recovered. Then, the obtained crystal was subjected to recrystallization refining with a hexane/ethyl acetate mixed solvent to thereby obtain a white crystal. The white crystal thus obtained was used as it was in the following step.

(3) The white crystal obtained in the above (2), and reagents and solvents described below were charged in a reaction vessel.
Chloroform: 100 ml
Pyridine: 150 ml
4-Methoxyphenol: 0.2 g
N,N-dimethylaminopyridine: 1.2 g
Anhydrous methacrylic acid: 30 ml Then, the reaction solution was stirred at room temperature for 12 hours. At this time, the degree of the reaction progress was checked on occasion by TLC. Then, a 2N hydrochloric acid was added to suspend the reaction, and thereafter, an organic layer was extracted with toluene. Then, the obtained organic layer was washed with a 2N hydrochloric acid and 10% sodium hydroxide aqueous solutions, water and saturated brine in order, and thereafter dried with anhydrous magnesium sulfate. Then, a crude product obtained by concentrating the organic layer under reduced pressure was refined by column chromatography to thereby obtain an oily product. Then, the oily product was subjected to recrystallization refining with a hexane/ethyl acetate mixed solvent to thereby obtain 26 g (yield: 55%) of 4,4'-bis((3-(2-methacryloyloxyethoxy)methyl)-4-methoxyphenyl)diphenyl sulfone.

The obtained compound was checked for the structure by $^1$H-NMR.

¹H-NMR (CDCl₃; TMS): δ 1.89 (s, 6H), 3.78 (t, 4H), 3.87 (s, 6H), 4.35 (t, 4H), 4.65 (s, 4H), 5.49 (br, 2H), 6.09 (br, 2H), 6.90-6.98 (m, 2H), 7.45-7.51 (m, 2H), 7.60-7.72 (m, 8H), 7.94-8.02 (m, 4H)

Comparative Example 2

A specific synthesis method of a compound synthesized in Comparative Example 2 will be described below.

(1) A product of a light yellow liquid was obtain by the same method as in Comparative Example 1 (1), except for using 2-(4-chlorobutoxy)tetrahydro-2H-pyran (9.0 ml) shown below in place of 2-(2-buromoethoxy)tetrahydro-2H-pyran in Comparative Example (1). In the present Comparative Example, the amounts of sodium hydride (55%) and the intermediate compound D4 used were 2.8 g and 8.0 g, respectively. The light yellow liquid thus obtained was used as it was in the following step.

Formula 14

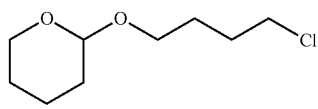

(2) A white crystal was obtained by the same method as in Comparative Example 1 (2), except for using the light yellow liquid obtained in the present Comparative Example (1) in place of using, in Comparative Example 1 (2), the light yellow liquid obtained in Comparative Example 1 (1). The white crystal thus obtain was used as it was in the following step.

(3) 6.7 g (yield: 53%) of a compound shown below, that is, 4,4'-bis((3-(4-methacryloyloxybutoxy)methyl)-4-methoxyphenyl)diphenyl sulfone, was obtained by the same method as in Comparative Example 1 (2), except for using the white crystal obtained in the present Comparative Example (2) in place of using, in Comparative Example 1 (3), the white crystal obtained in Comparative Example 1 (2).

Formula 15

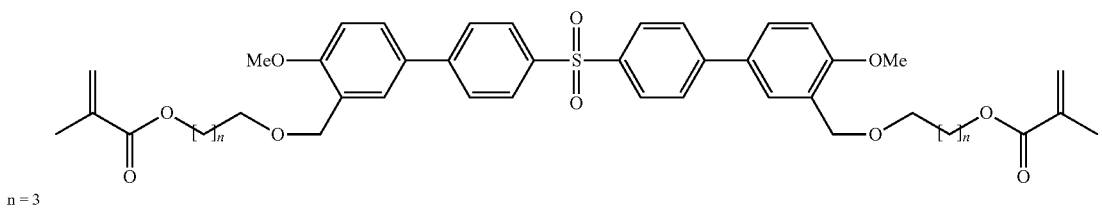

n = 3

The obtained compound was checked for the structure by ¹H-NMR.

¹H-NMR (CDCl₃; TMS): δ 1.89 (s, 6H), 2.24 (dt, 4H), 3.73 (t, 4H), 3.85 (s, 6H), 4.32 (t, 4H), 4.65 (s, 4H), 5.49 (br, 2H), 6.09 (br, 2H), 6.91-6.99 (m, 2H), 7.45-7.52 (m, 2H), 7.59-7.72 (m, 8H), 7.93-8.02 (m, 4H)

Comparative Example 3

A synthesis scheme of a compound synthesized in Comparative Example 3 will be show below. A specific synthesis method will be described below.

Formula 16

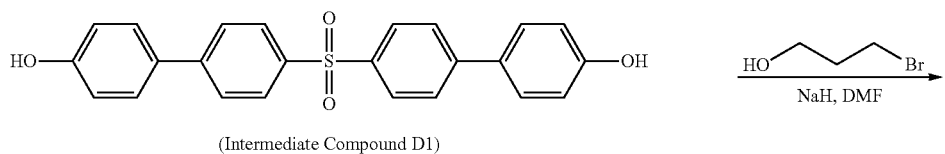

(Intermediate Compound D1)

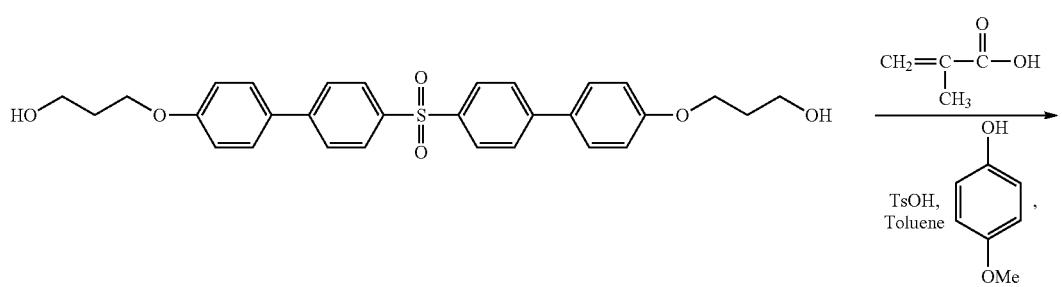

-continued

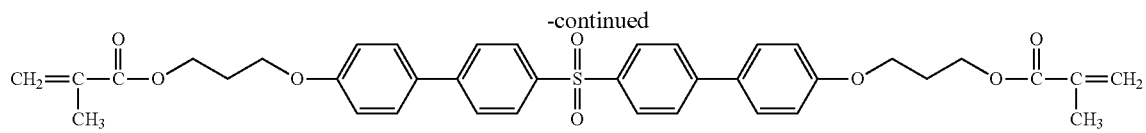

(1) A reagent and a solvent described below were charged in a reaction vessel.
Sodium hydride (55%): 2.5 g
N,N-dimethylformamide: 200 ml
Then, the reaction solution was cooled to 0° C., and thereafter, the intermediate compound D1 (10 g) was slowly added. Then, the reaction solution was stirred while being heated to room temperature. Then, 5.4 ml of 3-bromopropanol was added, and thereafter, the reaction solution was heated to 50° C., and stirred at the temperature (50° C.) for 12 hours. At this time, the degree of the reaction progress was checked on occasion by TLC. Then, the reaction was suspended by water, and thereafter, an organic phase was extracted with ethyl acetate. Then, the obtained organic layer was washed with water and saturated brine in order, and dried with anhydrous magnesium sulfate. Then, a crude product obtained by concentrating the organic phase under reduced pressure was recrystallized with a hexane/ethyl acetate mixed solvent to thereby obtain a white crystal. The white crystal thus obtained was used as it was in the following step.

solution was added to neutralize the reaction solution, and thereafter, an organic phase was extracted with chloroform. Then, the obtained organic phase was washed with water and saturated brine in order, and thereafter dried with anhydrous magnesium sulfate. Then, a crude product obtained by concentrating the organic layer under reduced pressure was refined by column chromatography to thereby obtain 1.9 g (yield: 55%) of 4,4'-bis(4-(3-methacryloyloxypropoxy)phenyl)diphenyl sulfone.
The obtained compound was checked for the structure by $^1$H-NMR.
$^1$H-NMR (CDCl$_3$; TMS): δ 1.94 (s, 6H), 2.19 (dt, 4H), 4.11 (t, 4H), 4.36 (t, 4H), 5.56 (br, 2H), 6.11 (br, 2H), 6.94-6.99 (m, 4H), 7.45-7.54 (m, 4H), 7.63-7.69 (m, 4H), 7.96-8.03 (m, 4H)

Comparative Example 4

A synthesis scheme of a compound synthesized in Comparative Example 4 will be show below. A specific synthesis method will be described below.

Formula 17

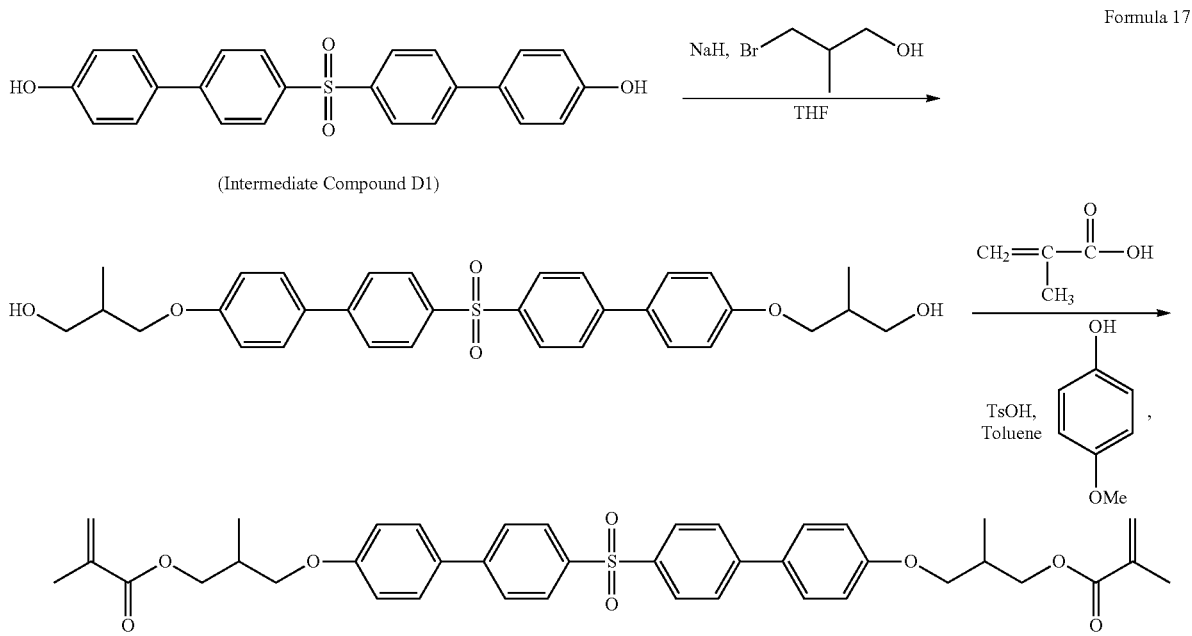

(2) Reagents and a solvent described below were charged in a reaction vessel.
The white crystal obtained in (1) in the present Comparative Example: 3.0 g
Methacrylic acid: 30 ml
Para-toluenesulfonic acid: 0.2 g
4-Methoxyphenol: 0.2 g
Toluene: 30 ml
Then, the reaction solution was heated and stirred for 20 hours. Here, moisture produced at this time was suitably removed, and the degree of the reaction progress was checked on occasion by TLC. Then, a sodium hydroxide aqueous (1) A reagent and a solvent described below were charged in a reaction vessel.
Sodium hydride (55%): 2.5 g
N,N-dimethylformamide: 200 ml
Then, the reaction solution was cooled to 0° C., and thereafter, the intermediate compound D1 (10 g) was slowly added. Then, the reaction solution was stirred while being heated to room temperature. Then, 6.0 ml of 3-bromo-2-methylpropanol was added, and thereafter, the reaction solution was heated to 50° C., and stirred at the temperature (50° C.) for 12 hours. At this time, the degree of the reaction progress was checked on occasion by TLC. Then, the reaction was suspended by water, and thereafter, an organic phase was extracted with ethyl acetate. Then, the obtained organic layer was washed with water and saturated brine in order, and thereafter dried with anhydrous magnesium sulfate. Then, a crude product obtained by concentrating the organic phase under reduced pressure was recrystallized with a hexane/ethyl acetate mixed solvent to thereby obtain a white crystal. The white crystal thus obtained was used as it was in the following step.

(2) Reagents and a solvent described below were charged in a reaction vessel.

The white crystal obtained in (1) in the present Comparative Example: 3.0 g

Methacrylic acid: 30 ml

Para-toluenesulfonic acid: 0.2 g

4-Methoxyphenol: 0.2 g

Toluene: 30 ml

Then, the reaction solution was heated and stirred for 20 hours. Here, moisture produced at this time was suitably removed, and the degree of the reaction progress was checked on occasion by TLC. Then, a sodium hydroxide aqueous solution was added to neutralize the reaction solution, and thereafter, an organic phase was extracted with chloroform. Then, the obtained organic phase was washed with water and saturated brine in order, and thereafter dried with anhydrous magnesium sulfate. Then, a crude product obtained by concentrating the organic layer under reduced pressure was refined by column chromatography to thereby obtain 2.2 g (yield: 60%) of 4,4'-bis(4-(3-methacryloyloxy-2-methylpropoxy)phenyl)diphenyl sulfone.

The obtained compound was checked for the structure by $^1$H-NMR.

$^1$H-NMR (CDCl$_3$; TMS): δ 1.23 (s, 6H), 2.56 (m, 2H), 2.83 (s, 6H) 3.95 (d, 4H), 4.18 (d, 4H), 5.56 (m, 2H), 6.11 (m, 2H), 6.92-6.98 (m, 4H), 7.35-7.49 (m, 4H), 7.59-7.62 (m, 4H), 7.90-7.93 (m, 4H)

Comparative Example 5

A synthesis scheme of a compound synthesized in Comparative Example 5 will be show below. A specific synthesis method will be described below.

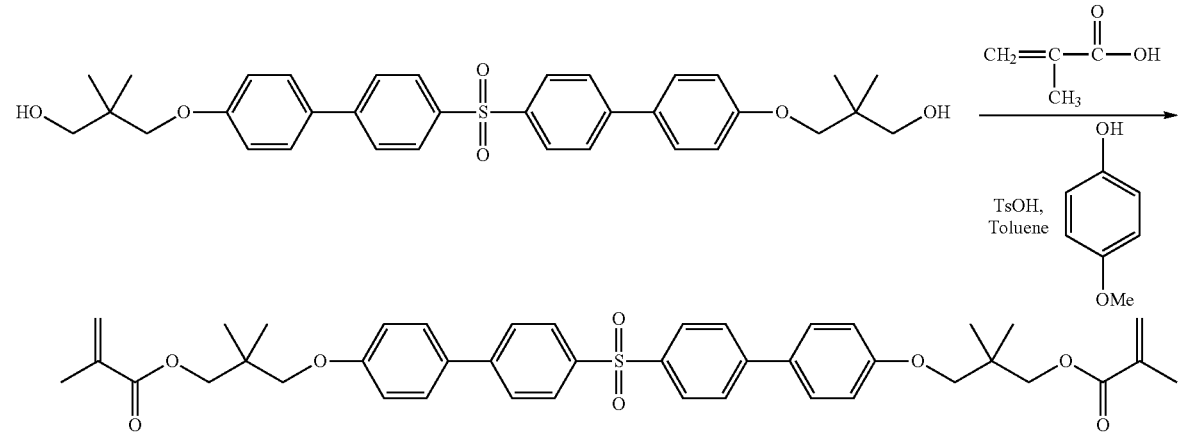

Formula 18

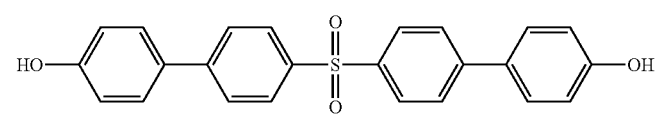
(Intermediate Compound D1)

(1) A reagent and a solvent described below were charged in a reaction vessel.

Sodium hydride (55%): 2.5 g

N,N-dimethylformamide: 200 ml

Then, the reaction solution was cooled to 0° C., and thereafter, the intermediate compound D1 (10 g) was slowly added. Then, the reaction solution was stirred while being heated to room temperature. Then, 6.5 ml of 3-bromo-2,2-dimethylpropanol was added, and thereafter, the reaction solution was heated to 50° C., and stirred at the temperature (50° C.) for 12 hours. At this time, the degree of the reaction progress was checked on occasion by TLC. Then, the reaction was suspended by water, and thereafter, an organic phase was extracted with ethyl acetate. Then, the obtained organic layer was washed with water and saturated brine in order, and thereafter dried with anhydrous magnesium sulfate. Then, a crude product obtained by concentrating the organic phase under reduced pressure was recrystallized with a hexane/ethyl acetate mixed solvent to thereby obtain a white crystal. The white crystal thus obtained was used as it was in the following step.

(2) Reagents and a solvent described below were charged in a reaction vessel.

The white crystal obtained in (1) in the present Comparative Example: 3.0 g

Methacrylic acid: 30 ml

Para-toluenesulfonic acid: 0.2 g

4-Methoxyphenol: 0.2 g

Toluene: 30 ml

Then, the reaction solution was heated and stirred for 20 hours. Here, moisture produced at this time was suitably removed, and the degree of the reaction progress was checked on occasion by TLC. Then, a sodium hydroxide aqueous solution was added to neutralize the reaction solution, and thereafter, an organic phase was extracted with chloroform. Then, the obtained organic phase was washed with water and saturated brine in order, and thereafter dried with anhydrous magnesium sulfate. Then, a crude product obtained by concentrating the organic layer under reduced pressure was refined by column chromatography to thereby obtain 1.8 g (yield: 48%) of 4,4'-bis(4-(3-methacryloyloxy-2,2-dimethylpropoxy)phenyl)diphenyl sulfone.

The obtained compound was checked for the structure by $^1$H-NMR.

$^1$H-NMR (CDCl$_3$; TMS): δ 1.18 (s, 12H), 2.23 (s, 6H) 3.96 (d, 4H), 4.20 (d, 4H), 5.55 (m, 2H), 6.12 (m, 2H), 6.90-6.97 (m, 4H), 7.36-7.50 (m, 4H), 7.60-7.66 (m, 4H), 7.88-7.95 (m, 4H)

Comparative Example 6

A synthesis scheme of a compound synthesized in Comparative Example 6 will be show below. A specific synthesis method will be described below.

obtained organic phase was washed with water and saturated brine in order, and thereafter dried with anhydrous magnesium sulfate. Then, the organic phase was concentrated under reduced pressure to thereby obtain a crude product. The obtained crude product was refined by silica gel chromatography to thereby obtain 7.4 g (yield: 60%) of a light yellow liquid.

(2) 5.0 g of the diol synthesized in (1) of the present Comparative Example, 20 ml of chloroform, 20 mg of MEHQ and 10 ml of pyridine were charged in a reaction vessel. The reaction vessel was cooled to 0° C., and 2.5 ml of methacryloyl chloride was dropwise charged. The reaction liquid was diluted with 30 ml of toluene, and thereafter, the reaction was suspended by a 2N hydrochloric acid aqueous solution; and an obtained organic layer was washed with an acidic and basic aqueous solutions, and thereafter dried with saturated brine and anhydrous magnesium sulfate. A crude product obtained by removing the solvent was refined by silica gel chromatography to thereby obtain 2.4 g (yield: 40%) of 4,4'-bis((3-(2-methacryloyloxycyclohexyloxy)methyl)-4-methoxyphenyl)diphenyl sulfone.

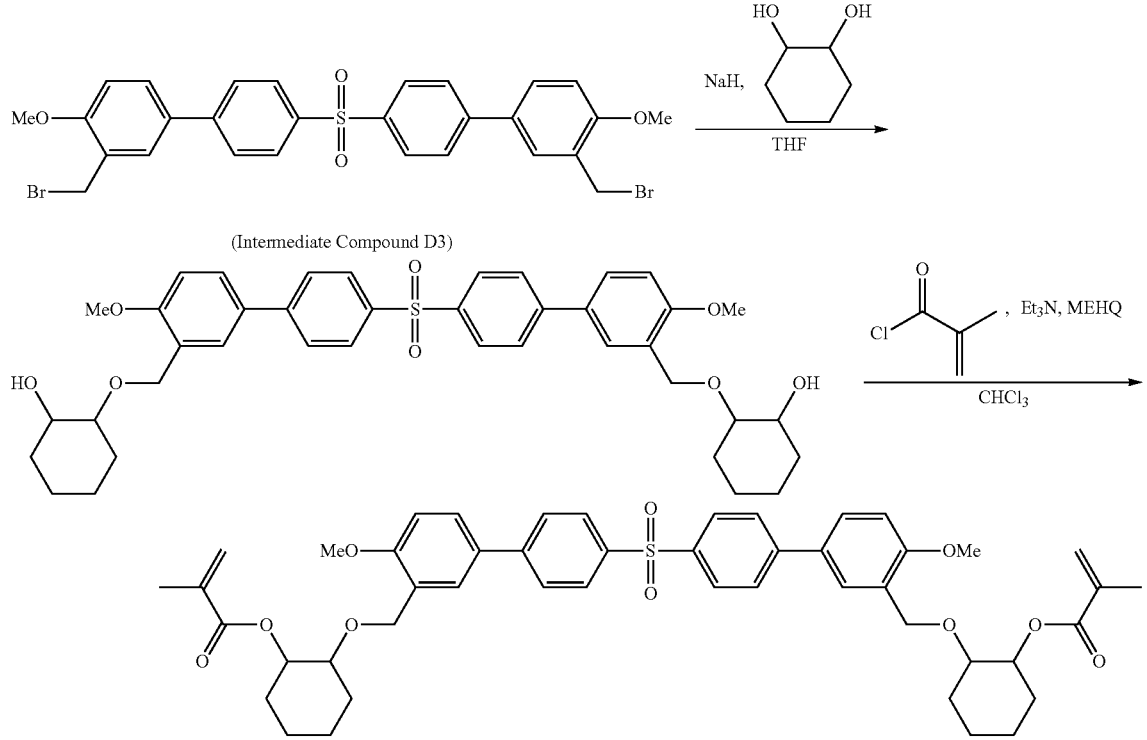

Formula 19

(1) A reagent and a solvent described below were charged in a reaction vessel.

Sodium hydride: 2.5 g
THF: 0.1 L

Then, the reaction vessel was cooled to 0° C., and a liquid of 17 g of 1,2-cyclohexanediol diluted with 40 mL of THF was slowly dropwise charged. After the completion of the dropwise charging, the reaction vessel was heated to 20° C., and the mixture was stirred further for 1 hour. The intermediate compound D3 (10 g) was added thereto at one time, and the reaction vessel was heated to 60° C. and the mixture was stirred for 5 hours. The reaction was suspended by water; an organic phase was extracted with ethyl acetate; thereafter, the The obtained compound was checked for the structure by $^1$H-NMR.

$^1$H-NMR (CDCl$_3$; TMS): δ 1.41-2.01 (m, 22H), 3.80 (d, 4H), 3.98 (s, 6H), 4.08 (d, 4H), 5.52 (m, 2H), 6.07 (m, 2H), 6.91-6.96 (m, 4H), 7.37-7.52 (m, 4H), 7.58-7.67 (m, 4H), 7.87-7.96 (m, 4H)

Example 4

5% by mass of 1,6-hexanediol diacrylate and 500 ppm of 4-methoxyphenol were added to the compound synthesized in Example 2, and stirred at 80° C. for 30 min to thereby obtain a material in the form of the above-mentioned (B).

Evaluations of Optical Properties

The compounds synthesized in the Examples and the Comparative Examples were evaluated for the optical properties by methods described below.

(1) Fabrication of Samples for Evaluation

Samples for evaluation were fabricated by the following methods.

(1a) Samples for Measuring the Refractive Index

Two plates of glass substrates of a circular plate type having a diameter of 20 mm were prepared; and an optical composition to become a measurement object containing a (meth) acrylate compound, a polymerization inhibitor and a polymerization initiator was mounted on a first plate of the glass substrates so that the thickness uniformly became 500 μm. Then, a second plate of the glass substrates was placed on the optical composition to become a measurement object, and the outer periphery of the glass substrates was then sealed. Here, in the case where the optical composition to become a measurement object was in the form of the above-mentioned (A) or (B), the sample was irradiated with ultraviolet light to thereby cure the optical composition interposed between the two plates of the glass substrates. The optical composition to become a measurement object was in the form of the (A) for Examples 1 to 3 and Comparative Examples 1 to 6, and in the form of the (B) for Example 4.

(1b) Samples for Measuring the Transmittance Samples were fabricated by the same method as in the above (1a), except for preparing glass substrates of a circular plate type having a diameter of 50 mm, and preparing both of samples having a thickness of 500 μm of the optical composition to become a measurement object mounted on the first plates of the glass substrates and samples having a thickness of 1,000 μm thereof.

(2) Measurements and Evaluations

The refractive index and the birefringence were measured using an Abbe refractometer (Kalnew Optical Industrial Co., Ltd.), and birefringences at a wavelength of 587.6 nm are shown in Table.

Two kinds of films having different optical path lengths were formed and measured for the transmittances, respectively, using a spectrophotometer U-4000 (product name) made by Hitachi High-Technologies Corp. The results at 410 nm in terms of internal transmittance (500 μm) are shown in Table 1.

The cases of having an optical property in the B range in FIG. 1, a transmittance at 410 nm of 90% or more, and a birefringence of less than 0.001 are defined as comprehensive evaluation A; and the other cases are defined as comprehensive evaluation C. The results are shown in Table 1.

TABLE 1

|  | nd | vd | θ g, F | Transmittance | Birefringence | Comprehensive Evaluation |
|---|---|---|---|---|---|---|
| Example 1 | 1.61 | 20.5 | 0.72 | 98 | 0.0005 | A |
| Example 2 | 1.61 | 20.6 | 0.71 | 98 | 0.0007 | A |
| Example 3 | 1.60 | 20.8 | 0.71 | 98 | 0.0007 | A |
| Example 4 | 1.60 | 20.9 | 0.71 | 98 | 0.0005 | A |
| Comparative Example 1 | 1.62 | 19.5 | 0.72 | 98 | 0.0014 | C |
| Comparative Example 2 | 1.61 | 20.5 | 0.72 | 98 | 0.0013 | C |
| Comparative Example 3 | 1.62 | 19.3 | 0.71 | 98 | 0.0018 | C |
| Comparative Example 4 | 1.62 | 19.3 | 0.71 | 98 | 0.0015 | C |

TABLE 1-continued

|  | nd | vd | θ g, F | Transmittance | Birefringence | Comprehensive Evaluation |
|---|---|---|---|---|---|---|
| Comparative Example 5 | 1.62 | 19.2 | 0.71 | 98 | 0.0021 | C |
| Comparative Example 6 | 1.59 | 20.9 | 0.69 | 98 | 0.0013 | C |

Since a molded article and optical element prepared by molding the optical composition according to the present invention have a high dispersion property (Abbe number ($v_d$)) and secondary dispersion property (θg,F) (high θg,F property) of the refractive index, and have a low birefringence, the molded article and optical element have a high property of the chromatic aberration correction function. Therefore, the molded article and optical element can be utilized for apparatuses such as camera lenses having a plurality of lenses.

The present invention can provide a molded article having a high dispersion property (Abbe number ($v_d$)) and secondary dispersion property (θg,F) of the refractive index, and having a low birefringence and a high property of the chromatic aberration correction function, and an optical element using the same. The present invention can also provide an optical composition and a (meth)acrylate compound to provide the molded article.

Therefore, in an optical element having the molded article according to the present invention, the chromatic aberration can be removed efficiently. Therefore, the present invention can make optical systems of a more reduced weight and size.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-168135, filed on Jul. 30, 2012, which is hereby incorporated by reference herein in its entirety.

The invention claimed is:

1. An optical element comprising a molded article, wherein the molded article is prepared by molding a polymer prepared by polymerizing a (meth)acrylate compound represented at least by general formula (1):

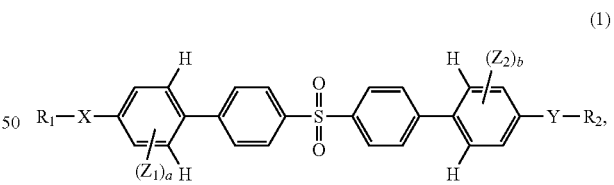

(1)

wherein a and b are each an integer of 1 or 2; X and Y are each —S— or —O—; $R_1$ and $R_2$ are each an alkyl group having 1 or 2 carbon atoms or a hydrogen atom; and $Z_1$ and $Z_2$ are each represented by general formula (2):

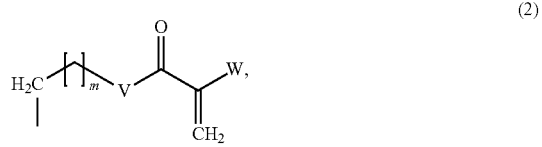

(2)

wherein m is selected from 0 and 1; W is a hydrogen atom or a methyl group; and V is selected from substituents represented by:

\*—O—$C_nH_{2n}$—O—\*\*;

\*—S—$C_nH_{2n}$—S—\*\*; and

\*—S—$C_nH_{2n}$—O—\*\*, wherein \* represents a bond with an alkyl group; \*\* represents a bond with a (meth)acryloyl group; n is selected from 2, 3 and 4; and at least one hydrogen atom of —$C_nH_{2n}$— is replaced by a methyl group.

2. The optical element according to claim 1, wherein the optical element is a lens.

3. The optical element according to claim 2, wherein the lens comprises a lens base material and the molded article provided on the lens base material.

4. The optical element according to claim 2, wherein the lens comprises two lens base materials and the molded article provided between the two lens base materials.

5. The optical element according to claim 1, wherein $R_1$ and $R_2$ are each an alkyl group having 1 or 2 carbon atoms.

6. The optical element according to claim 1, wherein X and Y are each —O—; and $R_1$ and $R_2$ are each an alkyl group having 1 or 2 carbon atoms.

7. The optical element according to claim 1, wherein V is a substituent represented by \*—O—$C_nH_{2n}$—O—\*\*.

8. The optical element according to claim 1, wherein m is 0.

9. The optical element according to claim 1, wherein a is 1 and b is 1.

10. An optical composition comprising a (meth)acrylate compound represented at least by general formula (1) and a polymerization initiator:

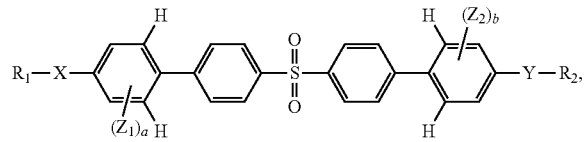

(1)

wherein a and b are each an integer of 1 or 2; X and Y are each —S— or —O—; $R_1$ and $R_2$ are each an alkyl group having 1 or 2 carbon atoms or a hydrogen atom; and $Z_1$ and $Z_2$ are each represented by general formula (2):

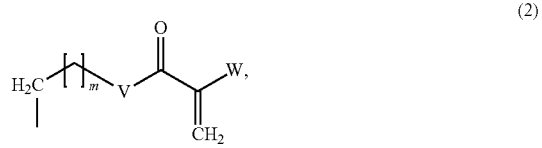

(2)

wherein m is selected from 0 and 1; W is a hydrogen atom or a methyl group; and V is selected from substituents represented by:

\*—O—$C_nH_{2n}$—O—\*\*;

\*—S—$C_nH_{2n}$—S—\*\*; and

\*—S—$C_nH_{2n}$—O—\*\*, wherein \* represents a bond with an alkyl group; \*\* represents a bond with a (meth)acryloyl group; n is selected from 2, 3 and 4; and at least one hydrogen atom of —$C_nH_{2n}$— is replaced by a methyl group.

11. The optical composition according to claim 10, wherein $R_1$ and $R_2$ are each an alkyl group having 1 or 2 carbon atoms.

12. The optical composition according to claim 10, wherein X and Y are each —O—; and $R_1$ and $R_2$ are each an alkyl group having 1 or 2 carbon atoms.

13. The optical composition according to claim 10, wherein V is a substituent represented by \*—O—$C_nH_{2n}$—O—\*\*.

14. The optical composition according to claim 10, wherein m is 0.

15. The optical composition according to claim 10, wherein a is 1 and b is 1.

16. A molded article prepared by molding a polymer of an optical composition according to claim 10.

17. A (meth)acrylate compound represented at least by general formula (1):

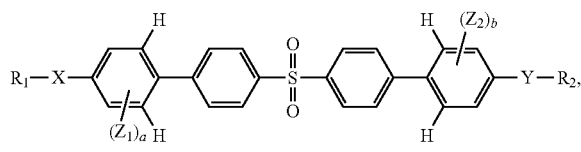

(1)

wherein a and b are each an integer of 1 or 2; X and Y are each —S— or —O—; $R_1$ and $R_2$ are each an alkyl group having 1 or 2 carbon atoms or a hydrogen atom; and $Z_1$ and $Z_2$ are each represented by general formula (2):

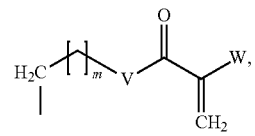

(2)

wherein m is selected from 0 and 1; W is a hydrogen atom or a methyl group; and V is selected from substituents represented by:

\*—O—$C_nH_{2n}$—O—\*\*;

\*—S—$C_nH_{2n}$—S—\*\*; and

\*—S—$C_nH_{2n}$—O—\*\*, wherein \* represents a bond with an alkyl group; \*\* represents a bond with a (meth)acryloyl group; n is selected from 2, 3 and 4; and at least one hydrogen atom of —$C_nH_{2n}$— is replaced by a methyl group.

\* \* \* \* \*